United States Patent
Itoh et al.

(10) Patent No.: US 10,360,459 B2
(45) Date of Patent: Jul. 23, 2019

(54) DETECTION DEVICE, DETECTION METHOD, AND NON-TRANSITORY COMPUTER-READABLE RECORDING MEDIUM STORING DETECTION PROGRAM

(71) Applicant: Panasonic Intellectual Property Management Co., Ltd., Osaka (JP)

(72) Inventors: Tatsuo Itoh, Osaka (JP); Koichi Kusukame, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 358 days.

(21) Appl. No.: 15/471,050

(22) Filed: Mar. 28, 2017

(65) Prior Publication Data

US 2017/0293812 A1    Oct. 12, 2017

Related U.S. Application Data

(60) Provisional application No. 62/318,899, filed on Apr. 6, 2016.

(30) Foreign Application Priority Data

Aug. 1, 2016 (JP) .................................. 2016-151590
Nov. 24, 2016 (JP) .................................. 2016-228373

(51) Int. Cl.
*G06K 9/00* (2006.01)
*G01S 7/41* (2006.01)
*G01N 21/21* (2006.01)
*G01N 21/3554* (2014.01)
(Continued)

(52) U.S. Cl.
CPC ......... *G06K 9/00798* (2013.01); *G01N 21/21* (2013.01); *G01N 21/314* (2013.01);
(Continued)

(58) Field of Classification Search
CPC .......... G06K 9/00798; G06K 9/00805; G01N 21/21; G01N 21/3554; G01N 2201/105; G02B 27/283; H04N 5/33; G01S 7/411
See application file for complete search history.

(56) References Cited

U.S. PATENT DOCUMENTS 5,557,261 A    9/1996  Barbour
5,841,538 A *  11/1998 Schoeffler .............. B64D 15/20
                                                      356/369
(Continued)

FOREIGN PATENT DOCUMENTS

JP     2005-043240     2/2005

OTHER PUBLICATIONS

The Extended European Search Report dated Jul. 3, 2017 for the related European Patent Application No. 17164978.3.

*Primary Examiner* — Joshua D Taylor
*Assistant Examiner* — Patrick A Ryan
(74) *Attorney, Agent, or Firm* — Greenblum & Bernstein, P.L.C.

(57) ABSTRACT

A detection device includes: a light source that emits, toward an object, light of a first wavelength band, and light of a second wavelength band that is less readily absorbed by water than the light of the first wavelength band; a polarization splitter that splits at least one of S-polarized light and P-polarized light from light that has been reflected or scattered at the object; a photoreceptor that receives light reflected or scattered at the object via the polarization splitter; and a control unit that determines a state of the object from information based on light received by the photoreceptor. The light emitted by the light source is random polarized light where the ratio of P-polarized light and S-polarized light is generally uniform.

27 Claims, 14 Drawing Sheets

(51) Int. Cl.

| | |
|---|---|
| *G02B 27/28* | (2006.01) |
| *H04N 5/225* | (2006.01) |
| *H04N 5/33* | (2006.01) |
| *G01N 21/31* | (2006.01) |
| *G08B 19/02* | (2006.01) |
| *B60W 40/06* | (2012.01) |
| *G01N 21/47* | (2006.01) |

(52) U.S. Cl.
CPC .......... *G01N 21/3554* (2013.01); *G01S 7/411* (2013.01); *G02B 27/283* (2013.01); *G06K 9/00805* (2013.01); *G08B 19/02* (2013.01); *H04N 5/2256* (2013.01); *H04N 5/33* (2013.01); *B60W 40/06* (2013.01); *G01N 2021/4792* (2013.01); *G01N 2201/0216* (2013.01); *G01N 2201/105* (2013.01)

(56) References Cited

U.S. PATENT DOCUMENTS

| | | | |
|---|---|---|---|
| 2008/0129541 A1 | 6/2008 | Lu et al. | |
| 2009/0315993 A1* | 12/2009 | Hirai | B82Y 20/00 348/148 |
| 2010/0085175 A1 | 4/2010 | Fridthjof | |
| 2013/0141577 A1* | 6/2013 | Yoo | G01S 17/88 348/148 |
| 2013/0342683 A1* | 12/2013 | Nelson | G01J 3/0278 348/135 |
| 2014/0049405 A1* | 2/2014 | Breuer | B60Q 9/00 340/905 |
| 2015/0212199 A1* | 7/2015 | Nakamura | G01W 1/00 342/118 |

* cited by examiner

OBJECT

DETECTION DEVICE, DETECTION METHOD, AND NON-TRANSITORY COMPUTER-READABLE RECORDING MEDIUM STORING DETECTION PROGRAM

BACKGROUND

1. Technical Field

The present disclosure relates to a detection device, a detection method, and a non-transitory computer-readable recording medium storing a detection program, that detects states of moisture, states of freezing, and so forth, of objects.

2. Description of the Related Art

There has conventionally been disclosed a road surface state detection sensor (an example of a detection device) having a light source that emits light onto a road surface (an example of an object), a light detection unit that detects intensity of light (an example of a photoreception unit), a first analyzer (an example of a polarized light splitter) through which S-polarized light is transmitted, a second analyzer (an example of a polarized light splitter) through which P-polarized light is transmitted, and a signal processing unit (an example of a control unit) that processes output signals from the light detection unit (e.g., see Japanese Unexamined Patent Application Publication No. 2005-43240). This road surface state detection sensor identifies the state of the road surface based on relative light intensities among particular wavelengths in P-polarized light.

SUMMARY

In one general aspect, the techniques disclosed here feature a detection device including: a light source that emits, toward an object, light of a first wavelength band, and light of a second wavelength band that is less readily absorbed by water than the light of the first wavelength band; a polarization splitter that splits at least P-polarized light from light that includes S-polarized light and P-polarized light and that has been reflected or scattered at the object; a photoreceptor that receives light reflected or scattered at the object via the polarization splitter; and a control unit that determines a state of the object from information based on light received by the photoreceptor. The light emitted by the light source is random polarized light where the ratio of P-polarized light and S-polarized light is generally uniform.

According to the present disclosure, states of objects can be accurately detected.

It should be noted that general or specific embodiments may be implemented as a system, a method, an integrated circuit, a computer program, a recording medium such as a computer-readable CD-ROM or the like, or any selective combination of the system, method, integrated circuit, computer program, and recording medium.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
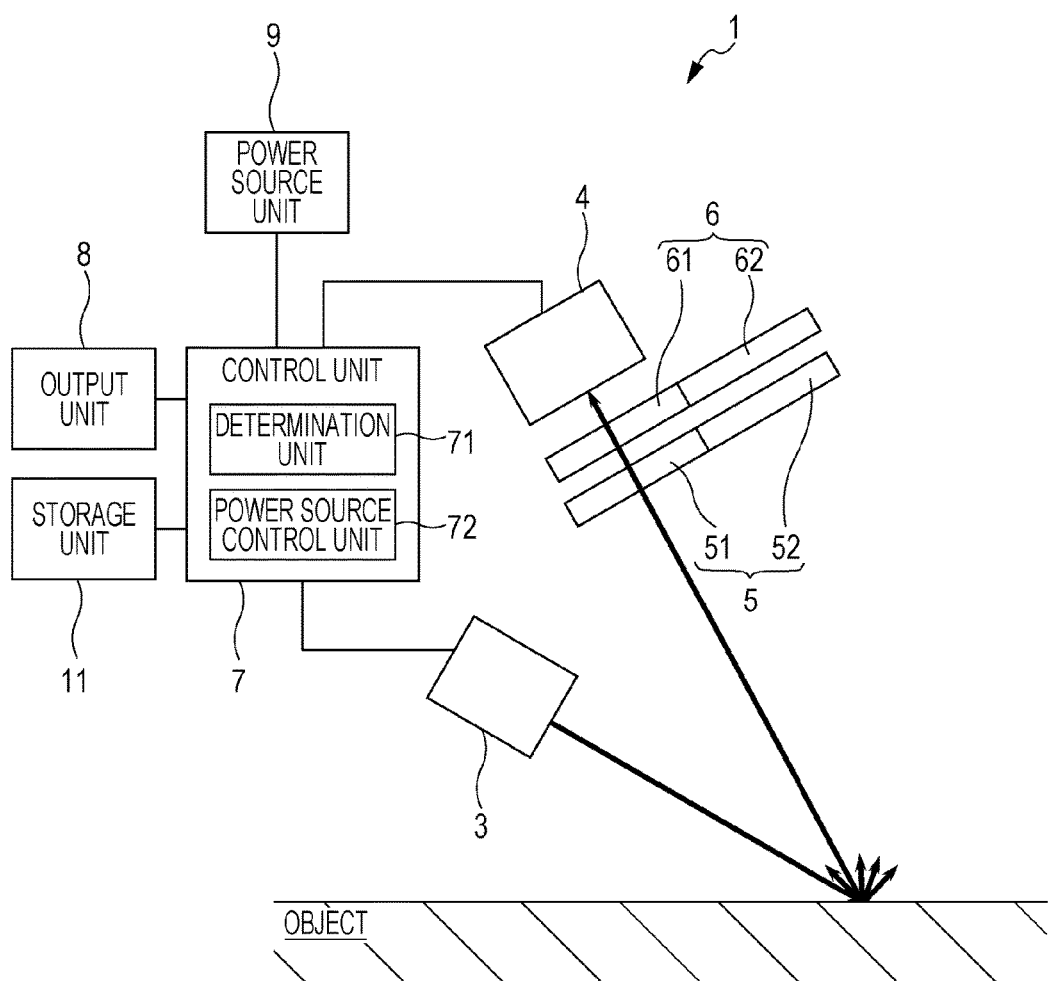
FIG. 1 is a schematic diagram illustrating a detection device according to a first embodiment.

Underlying Knowledge Forming Basis of the Present Disclosure

There currently is demand for a detection device that detects states of object, such as the amount of moisture and so forth. For example, in a case where a road surface outdoors is the object, there are four states of the road surface; a frozen state, a state under water, a state with snow accumulated, and a dry state, which the detection device has to identify.

Water has an absorption spectrum where light is absorbed at a particular wavelength region. Accordingly, the Present Inventors have taken note of the absorption spectrum of water as a way to detect the state of the road surface. In the relationship between wavelengths of light and absorption coefficient of water, water has peaks of light absorption (absorption peaks) near 740 nm, 980 nm, 1450 nm, and 1940 nm, in the near-infrared region of light (said to be 700 nm to 2500 nm), for example. Particularly, water has a nature where the longer the wavelength of light is at the absorption peak of light, the more readily light is absorbed. Accordingly, in principle, if light containing wavelengths near the absorption peak is cast on a road, the presence or absence of water or ice can be detected by the amount of reflected light thereof.

For example, in a case where the state of the road surface is under water, S-polarized light in the incident light to the water surface more readily exhibits normal reflection as compared to P-polarized light according to this nature. That is to say, the greater the incident angle is, the more readily the reflectance of S-polarized light increases in comparison with that of P-polarized light, and the less readily the reflectance of P-polarized light increases at the water surface in comparison with that of S-polarized light. Thus, P-polarized light entering the water surface is transmitted through the water, scattered at the road surface, and part of the light heads toward the light source side. According to this nature of light, if a photoreceptor is situated at the light source side, the amount of normally-reflecting S-polarized light received thereat will be smaller than the amount of received P-polarized light that has scattered at the object, for example.

On the other hand, when the road surface is in a frozen state, the surface of the ice is coarser than the surface of water, so more of both S-polarized light and P-polarized light is scattered at the surface as compared to the state where the road surface is under water. There is little difference between the amount of S-polarized light received and the amount of P-polarized light received when the photoreceptor is disposed at the side of the light source, unlike the case of the road surface being under water. That is to say, the ratio of the amount of S-polarized light received and the amount of P-polarized light received (intensity of S-polarized light/intensity of P-polarized light) is smaller than 1 in a frozen state, and is even smaller than that of the frozen state when the road surface is under water, so setting appropriate threshold values enables distinguishing whether the state is under water or frozen. It thus is conceivable that casting random polarized light, where the ratio of P-polarized light and S-polarized light is generally uniform in light containing wavelengths near peaks where water absorbs light, on the road surface, will enable detection of the state of the road surface by measuring the intensity of scattered light, and the proportions of P-polarized light and S-polarized light.

Further, when the intensity of scattered light in a state where the road surface is dry is set to 1, the intensity of scattered light is larger than 1 in a state where snow has accumulated. Accordingly, determination of whether the road surface is dry or snow has accumulated can be made simply by observing the intensity of scattered light.

It should be noted that simply finding light observed by an object cannot accurately detect the effects of the surface texture of the object or the effects of substances other than water that absorb light. Accordingly, a method called "dichroic spectrometry" is commonly used to suppress these influences. In dichroic spectrometry, the effects of surface texture and substances other than water that absorb light are compensated for by using light of a wavelength with little absorption, besides the absorption peak wavelengths where light is absorbed. Detection of the presence of water and ice using an intensity ratio between absorption peak wavelengths where light is absorbed and light of a wavelength with little absorption is preferable in the embodiments as well, instead of using intensity of scattered light.

Conventional detection devices identify the states of objects based on relative light intensity among wavelengths, from objects on which P-polarized light (linearly-polarized light) has been cast. On the other hand, there is demand to detect the states of objects (presence/absence of moisture, ice, etc., on objects) by a different way from the conventional detection device. There also is demand to accurately detect the states of objects using polarized light difference from the linearly-polarized light that is used in conventional detection devices. It has been found desirable to provide a detection device, a detection method, and a detection program, which can accurately detect states of objects.

Embodiments will be described below with reference to the drawings. It should be noted that each of the embodiments illustrated here is a specific exemplification of the present invention. Accordingly, values, shapes, materials, components, placements and connection states of components, and so forth, in the embodiments are only exemplary, and do not restrict the present disclosure. Components in the following embodiments, which are not included in an independent Claim indicating the highest concept of the present disclosure, are described as being optional components.

In the following description, the term "generally" is used as follows. For example, the term "generally the same" includes something being exactly the same, and also something that can be deemed to be substantially the same. The term "near" or "nearby" is also used in the same way.

It should be noted that the drawings are schematic diagrams, and are not necessarily exact illustrations. Configurations that are substantially the same in the drawings are denoted by the same reference numerals, and repetitive description will be omitted or simplified.

First Embodiment

A detection device according to a first embodiment of the present disclosure will be described.
Configuration First, the configuration of a detection device 1 according to the present embodiment will be described with reference to FIG. 1. FIG. 1 is a schematic diagram illustrating the detection device 1 according to the first embodiment. The detection device 1 is a device that casts light upon objects, and detects states of the objects, as illustrated in FIG. 1. An example of an object in the present embodiment is the road surface of a road. The states of the object are a snow-accumulated state, a dry state, an under-water state, and a frozen state of the road surface of the road.

The detection device 1 includes a light source 3, a photoreceptor 4, a polarization splitter 5, a wavelength separator 6, a control unit 7, an output unit 8, a power source unit 9, and a storage unit 11. Note that the light source 3, photoreceptor 4, polarization splitter 5, wavelength separator 6, control unit 7, output unit 8, power source unit 9, and storage unit 11 may be housed in an encasement omitted from illustration.

The light source 3 is a light-emitting module provided so as to emit light toward the object. The light emitted by the light source 3 is random polarized light where the ratio of P-polarized light and S-polarized light is generally uniform, and may be visible light, infrared light, or the like. The meaning of random polarized light that is generally uniform is that the oscillation direction of electric field in the light is random with components oscillating in various direction being present, meaning that randomly-oscillating components are uniform within an increment of time.

Infrared light is used in the present embodiment for the light. S-polarized light is light of a first wavelength band and light of a second wavelength band. P-polarized light is also light of a first wavelength band and light of a second wavelength band. The light of the second wavelength band has a wavelength band that is different from the first wavelength band, and has a nature of being less readily absorbed by water as compared with the first wavelength band. The light of the first wavelength band and the light of the second wavelength band are wavelength bands near absorption peaks where water readily absorbs light. Light having a wavelength λ1 is used as an example of the first wavelength band, and light having a wavelength λ2 is used as an example of the second wavelength band, in the light of the light source 3 according to the present embodiment. The light emitted by the light source 3 includes the light having the wavelength λ1 and the light having the wavelength λ2. Namely, the light source 3 simultaneously emits the light having the wavelength λ1 and the light having the wavelength λ2 toward the object. The light having the wavelength λ1 is random polarized light where the ratio of P-polarized light and S-polarized light is generally uniform. The light having the wavelength λ2 is random polarized light where the ratio of P-polarized light and S-polarized light is generally uniform.

The infrared light of the first wavelength band is light at an absorption peak regarding water, serving as an absorption wavelength of any one of near 740 nm, near 980 nm, near 1450 nm, and near 1940 nm. The infrared light of the second wavelength band is light of which the wavelength is shorter than the first wavelength band. For example, in a case where the infrared light of the first wavelength band is light near 980 nm, the infrared light of the second wavelength band may be light near 800 nm. In a case where the infrared light of the first wavelength band is light near 1940 nm, the infrared light of the second wavelength band may be light near 1550 nm.

Although a light source 3 that emits continuous-spectrum light, such as a halogen light or the like, may be used as the light source 3 for example, this is not restrictive. Examples of the light source 3 may include light emitting diode (LED) elements, semiconductor light-emitting elements such as semiconductor later or the like, electroluminescence (EL) elements such as organic EL and inorganic EL, and other solid-state light-emitting elements.

The photoreceptor 4 is installed facing the object, so as to receive light that has been emitted and scattered at the object. That is to say, the photoreceptor 4 is installed on the light source 3 side, and is not disposed so as to receive light from normal reflection of the light of the light source 3 off of the object. The photoreceptor 4 generates information relating to the quantity of received light. The photoreceptor 4 is an optical sensor such as an infrared sensor or the like, for example, but may be a camera.

Specifically, the photoreceptor 4 generates information P1, information P2, and information S1, and transmits to the control unit 7 as information relating to quantity of light. The information P1 is information based on light of P1 polarization intensity that is P-polarized light at wavelength λ1, which has passed through a P-polarizing filter S1 and a first wavelength separating filter 61. The information P2 is information based on light of P2 polarization intensity that is P-polarized light at wavelength λ2, which has passed through the P-polarizing filter 51 and a second wavelength separating filter 62. The information S1 is information based on light of S1 polarization intensity that is 5-polarized light at wavelength λ1, which has passed through an S-polarizing filter 52 and the first wavelength separating filter 61. Later-described information S2 is information based on light of S2 polarization intensity that is S-polarized light at wavelength λ2, which has passed through the S-polarizing filter 52 and second wavelength separating filter 62. Light of the wavelength λ1 is a wavelength that is more readily absorbed by water than the wavelength of the light of wavelength λ2 in the present embodiment. That is to say, the wavelength λ1 has a longer wavelength than the wavelength λ2 at the absorption peaks where water absorbs light. Note that the wavelength λ1 means light near the wavelength λ1. The same is true for wavelength λ2.

The polarization splitter 5 is disposed between the object and the photoreceptor 4, and functions to split predetermined polarized light from the light that has been scattered at the object. Examples of the polarization splitter 5 include a polarizing filter, a polarizing beam filter, and so forth. The polarization splitter 5 includes the P-polarizing filter 51 and the S-polarizing filter 52. The P-polarizing filter 51 has a nature of transmitting P-polarized light. The S-polarizing filter 52 has a nature of transmitting S-polarized light. The P-polarizing filter 51 and S-polarizing filter 52 are provided so as to be positionally interchangeable, by a driving unit that is omitted from illustration.

The wavelength separator 6 functions to separate wavelengths, so that only light of a predetermined wavelength band is transmitted. Although the wavelength separator 6 is positioned between the polarization splitter 5 and the photoreceptor 4 in the present embodiment, the wavelength separator 6 may be positioned between the object and the polarization splitter 5. The wavelength separator 6 includes the first wavelength separating filter 61 and second wavelength separating filter 62. The first wavelength separating filter 61 functions to transmit light near wavelength λ1. The second wavelength separating filter 62 functions to transmit light near wavelength λ2. The first wavelength separating filter 61 and second wavelength separating filter 62 also are provided so as to be positionally interchangeable, by a driving unit that is omitted from illustration.

The control unit 7 is electrically connected to the photoreceptor 4, light source 3, output unit 8, power source unit 9, and so forth. The control unit 7 receives information relating to the quantity of light that the photoreceptor 4 has received. The control unit 7 may adjust the output of light from the light source 3 base on this information relating to the quantity of light. The control unit 7 includes a determination unit 71 and a power source control unit 72. The determination unit 71 determines state of snow accumulated, dry state, state under water, and frozen state, of the object, based on the information P1, information P2, and information S1 received via the control unit 7. The power source control unit 72 effects control so that the light source 3 emits light.

The power source unit 9 is not restricted to a power source supplied from a primary battery or secondary battery, and may be a power source supplied from a power system, for example. The power source unit 9 is connected to the control unit 7 and supplies electric power to each of to the output unit 8, light source 3, and so forth, via the control unit 7.

The output unit 8 is a monitor such as a liquid crystal display, LED display, organic EL display, etc., a speaker that outputs audio and the like, and so forth, for example. The output unit 8 outputs the state of the object that the determination unit 71 has determined. Specifically, the output unit 8 outputs information regarding the snow-accumulated state, dry state, under-water state, or frozen state, at the object, which has been determined by the determination unit 71.

The storage unit 11 is a device where a control program executed by the control unit 7 is stored, in a case where the control unit 7 includes a processor, onboard computer, or the like. The storage unit 11 is realized by semiconductor memory, for example. The storage unit 11 may also store past information regarding the snow-accumulated state, dry state, under-water state, and frozen state, on objects in the past.

A method for this detection device 1 to determine the snow-accumulated state, dry state, under-water state, and frozen state, will now be described. Whether or not snow is accumulated on the object can be determined based on whether or not the reflectance of the information P2 is above a threshold value. This threshold value has been calculated based on reflectance values obtained by casting light on the surfaces of asphalt, concrete, white lines, yellow lines, and accumulated snow, in a case where the object is a road surface. These reflectance values are approximately 0.11 for asphalt, approximately 0.42 for concrete, approximately 0.63 for white lines, approximately 0.52 for yellow lines, and approximately 0.9 for accumulated snow. From these results, the threshold value was set to 0.8 in the present embodiment, as this is a value between the reflectance of white lines that has the highest reflectance other than accumulated snow, and the reflectance of accumulated snow. Note that this threshold value is only one example, and is not restrictive in particular. Any value may be used as long as it is a value between the reflectance of an object that has the highest reflectance other than accumulated snow and the reflectance of accumulated snow. The determination unit 71 determines whether or not the road surface state is a snow-accumulated state, by whether or not the information P2 is greater than the threshold value.

Determination of a dry state of the object can be made by whether or not the information P1 and information P2 are in approximation. The reason is that in a case where generally uniform random polarized light is cast upon an object in a dry state, both light of wavelength $\lambda 1$ and light of wavelength $\lambda 2$ are absorbed at the object by about the same amount. Accordingly, the quantity of light of the wavelength $\lambda 1$ and the quantity of light of the wavelength $\lambda 2$ are generally the same in the scattered light at the object. Note that the expression in the present embodiment that the information P1 and information P2 are in approximation means that the error of the information P1 and information P2 is within ±20%. This error range is preferable in a case where the object is a road surface, for example, since the information P1 and information P2 will differ depending on the road material.

Determination of whether the object is in a state under water can be made in the present embodiment by whether or not S2 polarization intensity (information S2)/P2 polarization intensity (information P2) is at or below a predetermined value. The reason is that the reflectance of S-polarized light is greater than that of P-polarized light when light of wavelength $\lambda 2$ enters water, so more P-polarized light is included in reflected light scattered at the water than S-polarized light. Now, S2 polarization intensity (information S2)/P2 polarization intensity (information P2) is smaller than 1 both in a case of a frozen state and a case of a state of being under water, but the state of being under water is even lower than the frozen state. That is to say, S2 polarization intensity (information S2)/P2 polarization intensity (information P2) is the ratio of S-polarized light in wavelength $\lambda 2$ and P-polarized light in wavelength $\lambda 2$ (a value obtained by dividing S2 polarization intensity by P2 polarization intensity). Accordingly, a frozen state and a case of a state of being under water can be distinguished by whether or not S2 polarization intensity (information S2)/P2 polarization intensity (information P2) is a predetermined value or lower. The predetermined value is 0.9 in the present embodiment. Distinguishing between a frozen state and a case of a state of being under water may be made by whether or not S1 polarization intensity (information S1)/P1 polarization intensity (information P1) is at or lower than a predetermined value, for example.

Determination of a frozen state of the object can be made using the method of determining a state of being under water, with determination being made that the object is in a frozen state where S2 polarization intensity (information S2)/P2 polarization intensity (information P2) is 1 or smaller but greater than 0.9.

Operations of Detection Device

Figure 2:
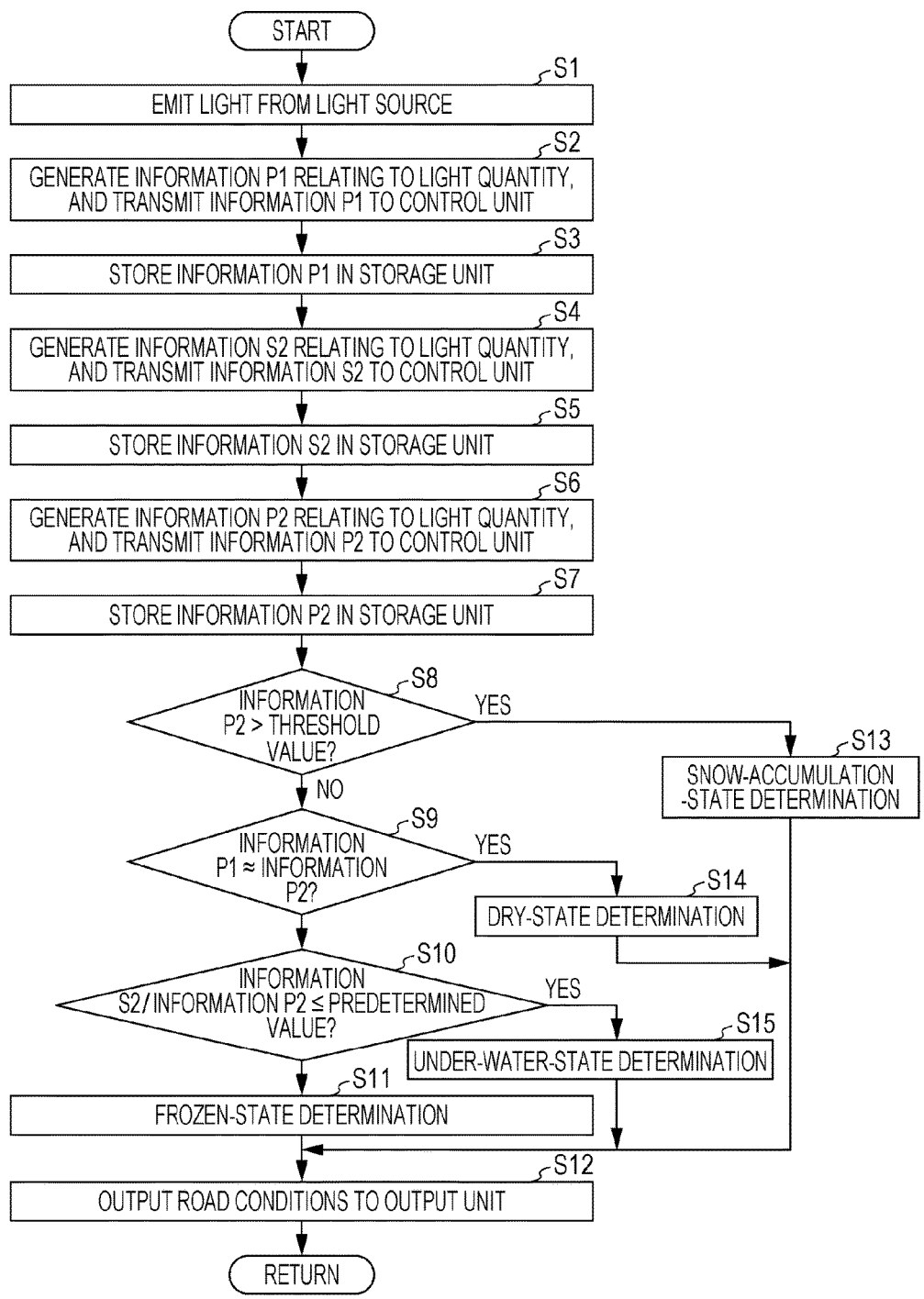
FIG. 2 is a flowchart illustrating operations of the detection device according to the first embodiment.

Next, an example of operations of the detection device 1, a detection method using the detection device 1, and a detection program that causes a computer to execute the detection method, will be described with reference to FIG. 2. FIG. 2 is a flowchart indicating operations of the detection device 1 according to the first embodiment.

In a case where light of P1 polarization intensity is to be received at the photoreceptor 4, the control unit 7 controls the driving unit so that the P-polarizing filter 51 and first wavelength separating filter 61 are situated between the photoreceptor 4 and the object, as illustrated in FIG. 1 for example. The control unit 7 then causes the light source 3 to emit light, which is cast on the object (step S1). The light cast on the object is scattered, and part of this light heads toward the photoreceptor 4. This light then passes through the P-polarizing filter 51 and first wavelength separating filter 61, becomes light of P1 polarization intensity, and is received at the photoreceptor 4. The photoreceptor 4 generates information P1 relating to the quantity of light that has been received, and transmits the information P1 to the control unit 7 (step S2).

The control unit 7 then receives the information P1 from the photoreceptor 4 (an example of acquiring), and stores the information P1 in the storage unit 11 (step S3).

Next, in a case where light of S2 polarization intensity is to be received at the photoreceptor 4, the control unit 7 controls the driving unit so that the S-polarizing filter 52 and second wavelength separating filter 62 are situated between the photoreceptor 4 and the object, for example. The light that is scattered at the object and heads toward the photoreceptor 4 passes through the S-polarizing filter 52 and second wavelength separating filter 62, becomes light of S2 polarization intensity, and is received at the photoreceptor 4. The photoreceptor 4 generates information S2 relating to the quantity of light that has been received, and transmits the information S2 to the control unit 7 (step S4).

The control unit 7 then receives the information S2 from the photoreceptor 4 (an example of acquiring), and stores the information S2 in the storage unit 11 (step S5).

Next, in a case where light of P2 polarization intensity is to be received at the photoreceptor 4, the control unit 7 controls the driving unit so that the P-polarizing filter 51 and second wavelength separating filter 62 are situated between the photoreceptor 4 and the object, for example. The light that is scattered at the object and heads toward the photoreceptor 4 through the P-polarizing filter 51 and second wavelength separating filter 62, becomes light of P2 polarization intensity, and is received at the photoreceptor 4. The photoreceptor 4 generates information P2 relating to the quantity of light that has been received, and transmits the information P2 to the control unit 7 (step S6).

The control unit 7 then receives the information P2 from the photoreceptor 4 (an example of acquiring), and stores the information P2 in the storage unit 11 (step S7).

The determination unit 71 determines whether or not the information P2 is greater than a predetermined threshold value (Step S8). In a case where the information P2 is greater than the threshold value (Yes in step S8), the determination unit 71 determines that the state of the object is a snow-accumulated state (step S13, example of snow-accumulation-state determination). The control unit 7 outputs the content of the determination made by the determination unit 71, that the state is a snow-accumulated state, to the output unit 8 (step S12). The flow then returns to the start, and repeats the same detection.

Now, determination may be made in step S8 regarding whether or not the information S2 is greater than a predetermined threshold value, instead of the information P2. In this case, an arrangement may be made where the light is made to pass through the S-polarizing filter 52 and second wavelength separating filter 62, light of S2 polarization intensity, which is S-polarized light that has wavelength $\lambda 2$, is extracted, the photoreceptor 4 generates information S2 relating to the quantity of light received, and the information S2 is transmitted to the control unit 7 in step S6. The control unit 7 may receive the information S2 from the photoreceptor 4 in step S7, and store the information S2 in the storage unit 11.

On the other hand, in a case where the information P2 is at or below the threshold value (NO in step S8), the determination unit 71 determines whether or not the information P1 and information P2 are in approximation (step S9). Alternatively, determination may be made in step S9 regarding whether or not the information S1 and information S2 are in approximation.

Specifically, in a case where the error between the information P1 and information P2 is within ±20% (YES in step S9), determination is made that the information P1 and information P2 are in approximation, and determination is made that the state of the object is a dry state (step S14, example of dry-state determination). In this case, the control unit 7 outputs the content of the determination made by the determination unit 71, that the state is a dry state, to the output unit 8 (step S12). The flow then returns to the start, and repeats the same detection.

On the other hand, in a case where the error between the information P1 and information P2 is not within ±20% (NO in step S9), the determination unit 71 determines whether or not S-polarized light (information S2)/P-polarized light (information P2) is at a predetermined value or lower (step S10). Although light of the wavelength $\lambda 1$ may be used in step S10, light of the wavelength $\lambda 2$ is less readily absorbed by water as compared to the light of the wavelength $\lambda 1$, and also the intensity of returning light to the photoreceptor 4 is greater and accordingly less readily affected by noise, so light of the wavelength $\lambda 2$ is preferably used.

Specifically, in a case where S-polarized light (information S2)/P-polarized light (information P2) is at a predetermined value (0.9 in the present embodiment) or below (YES in step S10), the determination unit 71 determines that the state of the object is under water (step S15, example of under-water-state determination). The control unit 7 then outputs the content of the determination made by the determination unit 71, that the state is under water, to the output unit 8 (step S12). The flow then returns to the start, and repeats the same detection.

An arrangement may also be made where, in step S9, the magnitude of information P1 and information P2 is determined. If the information P1 is smaller than a value obtained by multiplying information P2 by 100%-20%, the control unit 7 may determine that water exists, or possibly exists, at the object, from the information P1 which is P-polarized light that has low reflectance at water and is also light of wavelength $\lambda 1$ that is readily absorbed by water.

On the other hand, in a case where S-polarized light (information S2)/P-polarized light (information P2) is greater than the predetermined value (0.9 in the present embodiment) (NO in step S10), the determination unit 71 determines that the state of the object is frozen (step S11, example of frozen-state determination). The control unit 7 then outputs the content of the determination made by the determination unit 71, that the state is a frozen state, to the output unit 8 (step S12). The flow then returns to the start, and repeats the same detection.

Advantages of the First Embodiment

Advantages of the detection device 1, detection method, and detection program, according to the present embodiment, will now be described. As described above, the detection device 1 according to the present embodiment includes the light source 3 that emits, toward an object, light of wavelength $\lambda 1$ that is a first wavelength band, and light of wavelength $\lambda 2$ that is a second wavelength band less readily absorbed by water than the light of the wavelength $\lambda 1$ that is the first wavelength band, the polarization splitter 5 that splits at least P-polarized light from light that includes S-polarized light and P-polarized light and that has been reflected or scattered at the object, the photoreceptor 4 that receives light reflected or scattered at the object via the polarization splitter 5, and the control unit 7 that determines the state of the object from information based on light received by the photoreceptor 4. The light emitted by the light source 3 is random polarized light where the ratio of and P-polarized light is generally uniform.

According to this configuration, the control unit 7 can determine the state of the object by combining light of wavelength $\lambda 1$ that is the first wavelength band, light of wavelength $\lambda 2$ that is the second wavelength band, S-polarized light, and P-polarized light. Thus, the detection device 1 can accurately detect the state of the object by using polarized light that is different from a case of detecting the state of an object using linearly polarized light.

In the detection device 1 according to the present embodiment, the determination unit 71 of the control unit 7 acquires, from the photoreceptor 4, information based on S1 polarization intensity of S-polarized light of the wavelength $\lambda 1$ that is the first wavelength band, P1 polarization intensity of P-polarized light of the wavelength $\lambda 1$ that is the first wavelength band, S2 polarization intensity of S-polarized light of the wavelength $\lambda 2$ that is the second wavelength band, and P2 polarization intensity of P-polarized light of the wavelength $\lambda 2$ that is the second wavelength band. In a case where the S2 polarization intensity or the P2 polarization intensity is greater than a predetermined threshold value, the determination unit 71 of the control unit 7 determines that the state of the object is a snow-accumulated state. Further, in a case where the S1 polarization intensity and the S2 polarization intensity are generally equal, or the P1 polarization intensity and the P2 polarization intensity are generally equal, the determination unit 71 of the control unit 7 determines that the state of the object is a dry state. In a case where the P2 polarization intensity is greater than the S2 polarization intensity and also a value obtained by dividing the S2 polarization intensity by the P2 polarization intensity is equal to or smaller than a predetermined value, the control unit 7 determines that the state of the object is under water. In a case where the P2 polarization intensity is greater than the S2 polarization intensity and also a value obtained by dividing the S2 polarization intensity by the P2 polarization intensity is greater than a predetermined value, the determination unit 71 of the control unit 7 determines that the state of the object is a frozen state.

According to this configuration, the photoreceptor 4 can generate information P1, information P2, information S1, and information S2, from combinations of P-polarized light and S-polarized light, and wavelength λ1 and wavelength λ2. The determination unit 71 can determine the state of the object, which is snow-accumulated state, dry state, under-water state, or frozen state, from the received information (information P1, information P2, information S1, and information S2). Thus the state of the object can be detected in a sure manner.

The detection device 1 according to the present embodiment further has the wavelength separator 6 that separates light of the wavelength λ1 that is the first wavelength band and light of the wavelength λ2 that is the second wavelength band, from light reflected or scattered at the object. The wavelength separator 6 is disposed between the object and the photoreceptor 4.

According to this configuration, light of desired wavelengths can be extracted from light emitted by the light source 3. Thus, there is no need to prepare a light source 3 that emits light of the desired wavelength, and increase in manufacturing costs can be suppressed.

In the detection device 1 according to the present embodiment, light emitted from the light source 3 is infrared light. Infrared light of the wavelength λ1 that is the first wavelength band is light having an absorption peak of an absorption wavelength as to water out of one of near 740 nm, 980 nm, 1450 nm, and 1940 nm. Infrared light of the wavelength λ2 that is the second wavelength band is light of which the wavelength is shorter than the infrared light of the wavelength λ1 that is the first wavelength band.

According to this configuration, if light near 1940 nm is selected as the wavelength λ1 for example, absorption by water is high, is a high-sensitivity sensor is realized. If light near 980 nm is selected as the wavelength λ1, there is an advantage that a silicon photodetector can be used.

The detection method according to the present embodiment is for detecting a state of an object using the detection device 1. The determination unit 71 of the control unit 7 performs: acquiring, from a photoreceptor 4, information based on S1 polarization intensity of S-polarized light of the wavelength λ1 that is the first wavelength band, P1 polarization intensity of P-polarized light of the wavelength λ1 that is the first wavelength band, S2 polarization intensity of S-polarized light of the wavelength λ2 that is the second wavelength band, and P2 polarization intensity of P-polarized light of the wavelength λ2 that is the second wavelength band; determining, in a case where the S2 polarization intensity or the P2 polarization intensity is greater than a predetermined threshold value, that the state of the object is a snow-accumulated state; determining, in a case where the S1 polarization intensity and the S2 polarization intensity are generally equal, or the P1 polarization intensity and the P2 polarization intensity are generally equal, that the state of the object is a dry state; determining, in a case where the P2 polarization intensity is greater than the S2 polarization intensity and also a value obtained by dividing the S2 polarization intensity by the P2 polarization intensity is equal to or smaller than a predetermined value, that the state of the object is an under-water state; and determining, in a case where the P2 polarization intensity is greater than the S2 polarization intensity and also a value obtained by dividing the S2 polarization intensity by the P2 polarization intensity is greater than a predetermined value, that the state of the object is a frozen state.

This detection method yields the same advantages as the detection device 1 according to the present embodiment. A detection program according to the present embodiment causes a computer to execute this detection method. This detection program yields the same advantages as the detection device 1 according to the present embodiment.

Modification of First Embodiment

Figure 3:
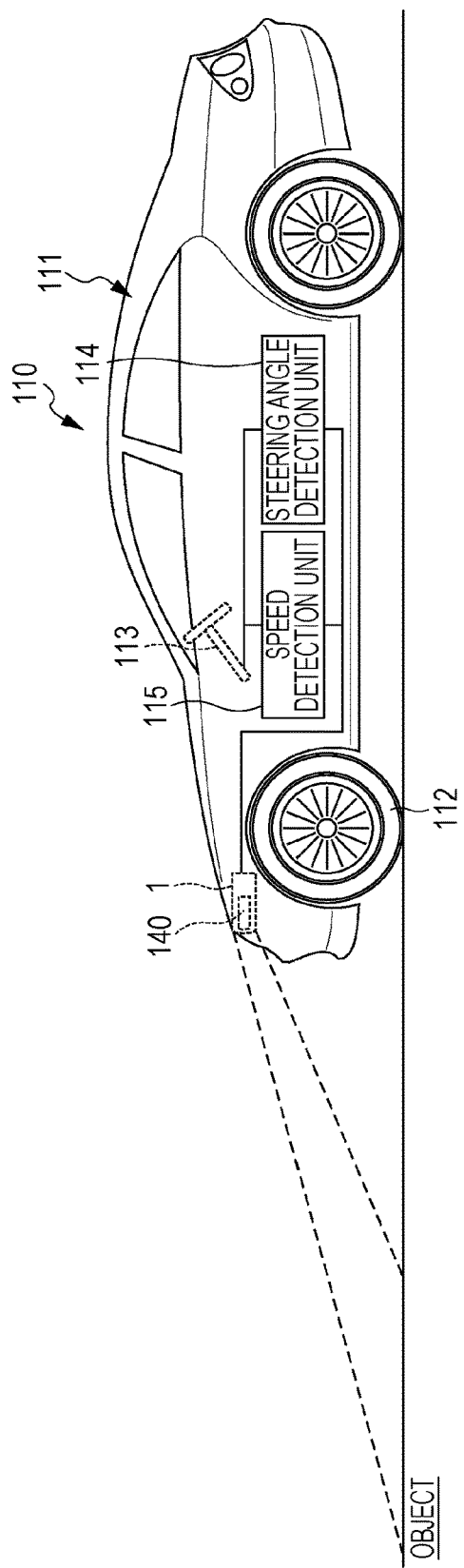
FIG. 3 is a schematic diagram illustrating a vehicle having a detection device according to a modification of the first embodiment.

A detection device 1 according to a modification of the first embodiment will be described with reference to FIG. 3. FIG. 3 is a schematic diagram illustrating a vehicle 110 including the detection device 1 according to the modification of the first embodiment. The modification of the first embodiment differs from the first embodiment in that a camera 140 is used as an example of the photoreceptor 4. Other configurations of the modification of the first embodiment are the same as in the first embodiment and so forth. Configurations that are the same are denoted by the same reference numerals, and detailed description regarding these configurations will be omitted.

The detection device 1 according to the modification of the first embodiment is installed in the vehicle 110, as illustrated in FIG. 3. The vehicle 110 includes a body 111, wheels 112, a steering wheel 113, a steering angle detection unit 114, and a speed detection unit 115.

The wheels 112, steering wheel 113, steering angle detection unit 114, speed detection unit 115, and so forth are provided to the body 111. The wheels 112 are steered by the steering wheel 113. The steering angle detection unit 114 is a sensor that detects the steering angle of the wheels 112, and is a steering angle sensor or the like that measures the amount of change in relative angle, for example. The steering angle detection unit 114 detects the steering angle of the wheels 112, and transmits detected steering angle information (an example of first information) to the control unit 7. The speed detection unit 115 is a sensor that detects the traveling speed of the vehicle 110, and is a speed detection sensor or the like, for example. The speed detection unit 115 detects the traveling speed of the vehicle 110, and transmits detected speed information (an example of second information) to the control unit 7.

When the light source 3 emits infrared light, the camera 140 generates a first image (an example of information) where the object has been imaged, and transmits this to the control unit 7. The state of the object, which is snow-accumulated state, dry state, under-water state, or frozen state, is in this first image. Examples of the object in this modification of the first embodiment include the road surface, a radiator grill of the automobile, etc.

When the light source 3 emits visible light, the camera 140 generates a second image (an example of information) where the object has been imaged, and transmits this to the control unit 7. This second image is a normal image of the object.

The control unit 7 generates a third image, where the first image is overlaid on the second image received from the camera 140, and outputs the third image to the output unit 8. Accordingly, an image of the object where the state thereof, which is snow-accumulated state, dry state, under-water state, or frozen state, has been added, is output to the output unit 8.

The camera 140 further generates a fourth image indicating the distance between the object and the camera 140, and transmits this to the control unit 7. This fourth image is an image having distance information.

The control unit 7 generates a fifth image, where the fourth image received from the camera 140 is overlaid on the third image, and outputs the fifth image to the output unit 8. And image where information indicating the distance between the object and the camera 140 has further been added to the image of the object where the state thereof, which is snow-accumulated state, dry state, under-water state, or frozen state, has been added, is output. Note that the first through fifth images may be still images or may be moving images.

The control unit 7 changes the position of imaging the object in accordance with the steering angle information of the wheels 112 and the speed information of the vehicle 110. For example, the light source 3 may be provided so as to be capable of rocking, to be able to change the optical axis direction (the direction in which light is emitted) of the light source 3. A drive mechanism may be used to realize rocking of the light source 3. The drive mechanism may be configured to change the attitude of the camera 140, polarization splitter 5, and wavelength separator 6 (in the case of the camera 140, changing the position that is imaged).

As an example of changing the position of imaging the object, the greater the steering angle of the wheels 112 is, the farther the object that the control unit 7 causes the camera 140 to image is from the detection device 1, in the traveling direction of the vehicle 110 that the steering angle detection unit 114 has detected from the steering angle of the wheels 112. Also, the faster the traveling speed of the vehicle 110 is, the farther from the detection device 1 the object that the control unit 7 causes the camera 140 to image is. There are cases where the greater the steering angle is, or the faster the traveling speed of the vehicle 110 is, the farther away the passenger (user) of the vehicle 110 will want to know the state of an object. The camera 140 may be made to image objects farther away from the detection device 1 in accordance with not only steering angle but also rate of increase of the steering angle (angular velocity of the steering angle).

An example of imaging a far object is to change the optical axis direction of the light source 3 that is currently casting light as the vehicle 110 travels, to be closer to horizontal, so that the light of the light source 3 is cast on an object that is farther on the optical axis of the light source 3 that the object where light is currently being cast.

Operations the same as in the flowchart in FIG. 2 are performed with this detection device 1 as well.

Advantages of the Modification of the First Embodiment

Advantages of the modification of the detection device 1 will now be described. As described above, the detection device 1 according to the modification of the present embodiment further includes the output unit 8 that outputs the state of the object. The light source 3 emits infrared light and visible light. The camera 140 generates the first image where the object is imaged when the light source 3 emits infrared light and the second image where the object is imaged when the light source 3 emits visible light, and transmits these to the determination unit 71 of the control unit 7. The determination unit 71 of the control unit 7 then generates the third image by overlaying the first image on the second image received from the camera 140, and outputs the third image to the output unit 8.

According to these configurations, the third image where the state of the object is added to a normal image of the object is output to the output unit 8, so information that is more readily comprehendible by the passenger can be provided. Accordingly, the passenger can instantly recognize the state of the object and make judgment, so danger avoidance of the vehicle 110 is facilitated.

In the detection device 1 according to the modification of the first embodiment, the camera 140 generates the fourth image indicating the distance between the object in the second image and the camera 140, and transmits to the determination unit 71 of the control unit 7. The determination unit 71 of the control unit 7 generates the fifth image where the fourth image received from the camera 140 is overlaid on the third image, and outputs the fifth image to the output unit 8.

According to this configuration, the fifth image where distance information has been added to the third information is output to the output unit 8, so information that is more readily comprehendible by the passenger can be provided. Accordingly, the passenger can instantly recognize the state of the object and make judgment, so danger avoidance of the vehicle 110 is facilitated.

The detection device 1 according to the modification of the first embodiment is installed in the vehicle 110. The vehicle 110 includes the wheels 112 steered by the steering wheel 113, the steering angle detection unit 114 that detects the steering angle of the wheels 112, and the speed detection unit 115 that detects the traveling speed of the vehicle 110. The steering angle detection unit 114 transmits first information relating to the steering angle of the wheels 112 to the control unit 7. The speed detection unit 115 transmits second information relating to the traveling speed of the vehicle 110 to the control unit 7. The control unit 7 then effects control to change the direction in which the light source 3 casts light and the position of the object to image, in accordance with the first information and second information.

According to this configuration, control unit 7 changes the direction of casting light and the position of the object to be imaged, in accordance with the traveling speed of the vehicle 110 and the steering angle of the steering wheel 113, so the state at a suitable position of the object can be detected.

In the detection device 1 according to the modification of the first embodiment, the control unit 7 effects control where the greater the steering angle of the wheels 112 is, the farther away from the detection device 1 the object caused to be imaged by the camera 140 is, in the direction of travel of the vehicle 110 that the steering angle detection unit 114 has detected from the steering angle of the wheels 112.

According to this configuration, a distant object is imaged in a case where the steering angle of the wheels 112 is great, so information that is more readily comprehendible by the passenger can be provided. Thus, the passenger can recognize the state of the object more readily.

In the detection device 1 according to the modification of the first embodiment, the control unit 7 effects control where the faster the traveling speed of the vehicle 110 is, the farther away from the detection device 1 the object caused to be imaged by the camera 140 is.

According to this configuration, a distant object is imaged in a case where the traveling speed of the vehicle 110 is fast, so information that is more readily comprehendible by the passenger can be provided. Thus, the passenger can recognize the state of the object more readily. Other advantages of the modification of the first embodiment are the same as the advantages of the first embodiment and so forth.

Second Embodiment

A detection device 200 according to a second embodiment will be described below.

Configuration

Figure 4:
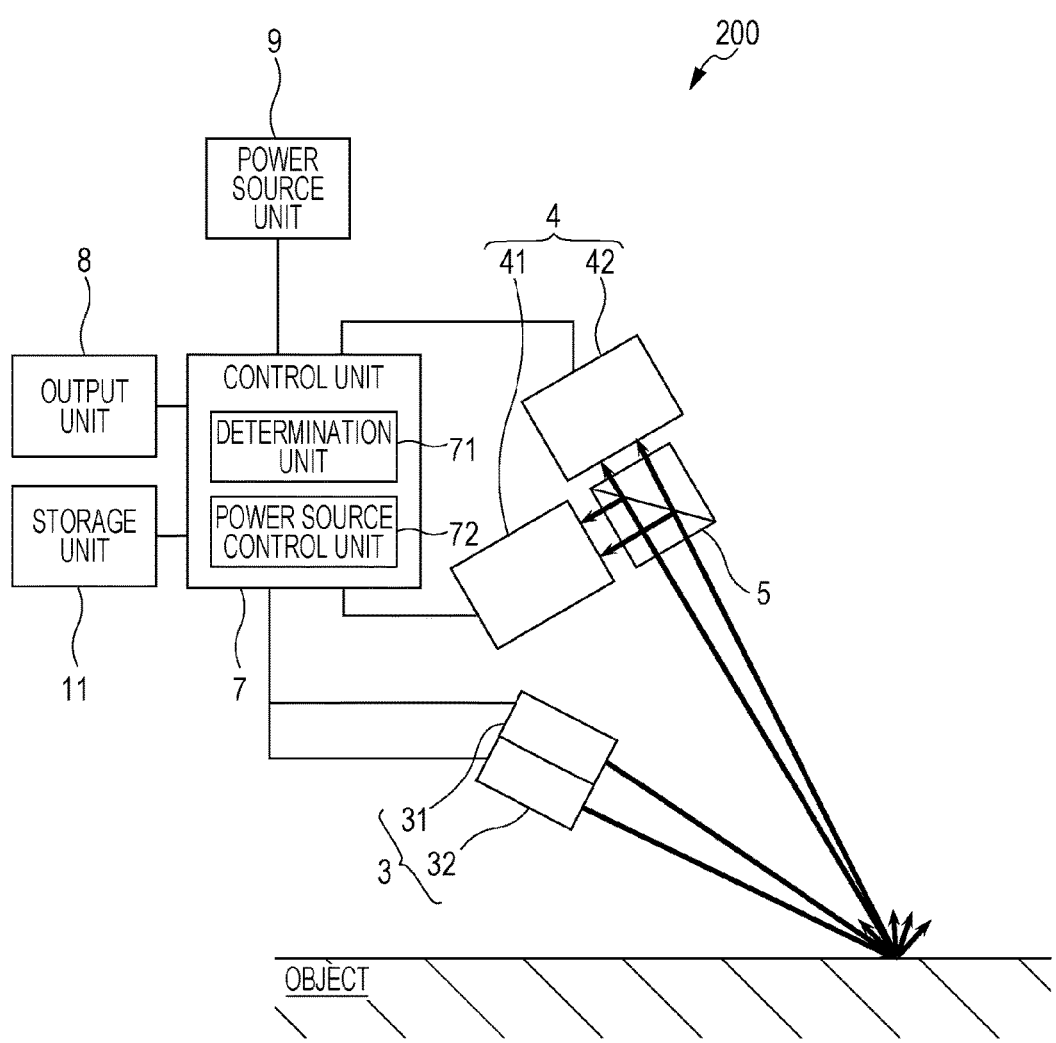
FIG. 4 is a schematic diagram illustrating a detection device according to a second embodiment.

The configuration of the detection device 200 according to the present embodiment will be described with reference to FIG. 4. FIG. 4 is a schematic diagram illustrating the detection device 200 according to the second embodiment.

Although one light source 3 was provided in the first embodiment, the detection device 200 according to the present embodiment differs from this in that two light sources 3 are provided. Another difference is the point that the detection device 200 according to the present embodiment is provided with a first photoreceptor 41 and a second photoreceptor 42, where as just one photoreceptor 4 is provided in the first embodiment. A further point of difference is that no wavelength separator 6 such as in the first embodiment is provided. Other configurations of the modification of the first embodiment are the same as in the first embodiment and so forth. Configurations that are the same are denoted by the same reference numerals, and detailed description regarding these configurations will be omitted.

The detection device 200 includes, in addition to the control unit 7 and polarization splitter 5, a first light source 31, a second light source 32, the first photoreceptor 41, and the second photoreceptor 42, as illustrated in FIG. 4. The polarization splitter 5 in the present embodiment is a polarization beam splitter capable of splitting into S-polarized light and P-polarized light.

Light emitted from the first light source 31 is random polarized light where the ratio of S-polarized light and P-polarized light is generally uniform, and is light of the first wavelength band. The wavelength of the first wavelength band is $\lambda 1$ in the present embodiment. Light emitted from the second light source 32 is random polarized light where the ratio of S-polarized light and P-polarized light is generally uniform, and is light of the second wavelength band. The wavelength of the second wavelength band is $\lambda 2$ in the present embodiment. The first light source 31 and second light source 32 are disposed so that the optical axes thereof intersect at the object. The first light source 31 and second light source 32 may each be the same light source 3 as in the first embodiment.

Of the light split by the polarization splitter 5, the first photoreceptor 41 receives the S-polarized light. Of the light split by the polarization splitter 5, the second photoreceptor 42 receives the P-polarized light. The first photoreceptor 41 and second photoreceptor 42 transmit information based on the received light to the control unit 7.

The power source control unit 72 of the control unit 7 effects control so that the first light source 31 emits light of wavelength $\lambda 1$, and so that the second light source 32 emits light of wavelength $\lambda 2$. The power source control unit 72 effects control so that the first light source 31 and second light source 32 alternately turn on and off.

Figure 5:
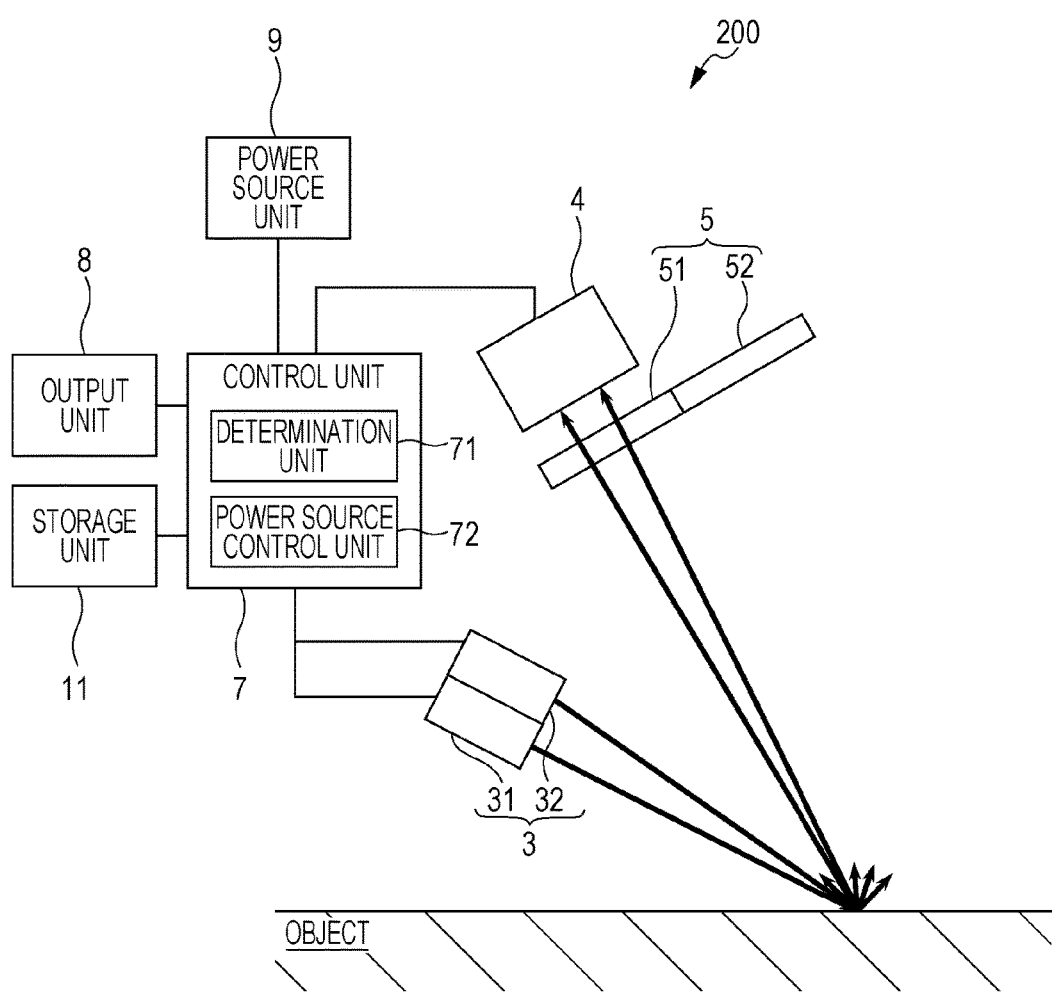
FIG. 5 is a schematic diagram illustrating the detection device according to the second embodiment.

FIG. 5 is a schematic diagram illustrating the detection device 200 according to the second embodiment. The polarization splitter 5 may be the S-polarizing filter 52 and P-polarizing filter 51 in the same way as the first embodiment, as illustrated in FIG. 5. In this case, a single photoreceptor 4 may be used, as in the first embodiment. Operations which are the same as in the flowchart in FIG. 2 are performed with this detection device 200 as well.

Advantages of Second Embodiment

Next, advantages of the detection device 200 according to the present embodiment are described. In the detection device 200 according to the present embodiment, the light source 3 includes the first light source 31 that emits light of the wavelength $\lambda 1$ that is the first wavelength band, and the second light source 32 that emits light of the wavelength $\lambda 2$ that is the second wavelength band as described above. The control unit 7 effects control so that the first light source 31 and second light source 32 alternately turn on and off. Accordingly, the light source 3 alternatively emits, toward the object, the light of the wavelength $\lambda 1$ and the light of the wavelength $\lambda 2$. Light reflected or scattered at the object is the light of the wavelength $\lambda 1$ when the light source 3 emits the light of the wavelength $\lambda 1$. On the other hand, light reflected or scattered at the object is the light of the wavelength $\lambda 2$ when the light source 3 emits the light of the wavelength $\lambda 2$.

According to this configuration, the first light source 31 emits light of the wavelength $\lambda 1$ and the second light source 32 emits light of the wavelength $\lambda 2$, so no wavelength separator 6 is necessary as in the first embodiment. Thus, the wavelength $\lambda 1$ and wavelength $\lambda 2$ each be received via the object, without having to provide a configuration to separate the wavelengths from the light of the light source 3. Accordingly, light of the wavelength $\lambda 1$ and wavelength $\lambda 2$ can be received via the object, without providing a configuration to separate the waveforms from the light source 3. Thus, increase in size of the detection device 200 can be suppressed. Other advantages of the present embodiment are the same as the advantages of the first embodiment and so forth.

Modification of Second Embodiment

Figure 6:
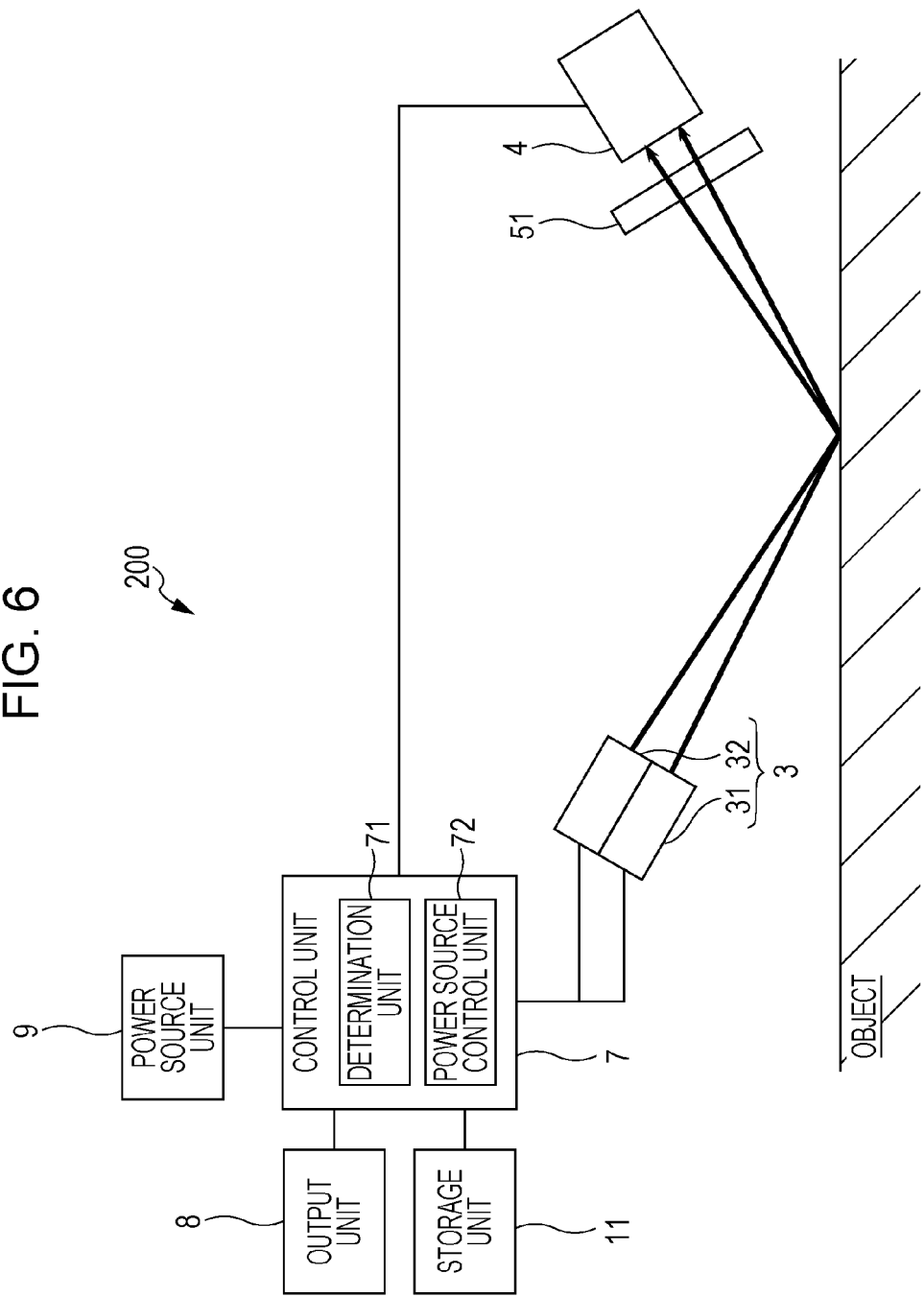
FIG. 6 is a schematic diagram illustrating a detection device according to a modification of the second embodiment.

A detection device 200 according to a modification of the second embodiment will be described with reference to FIG. 6. FIG. 6 is a schematic diagram illustrating the detection device 200 according to the modification of the second embodiment.

In the second embodiment, the photoreceptor 4 is disposed facing the object at the light source 3 side to receive emitted light scattered at the object, in the same way as in the first embodiment. However, the modification of the second embodiment differs from this in that the photoreceptor 4 is disposed so as to receive light of normal reflection of the emitted light at the object. Although the second embodiment uses the polarization splitter 5 to split light into P-polarized light and S-polarized light, in the modification of the second embodiment, the polarization splitter 5 uses only the P-polarizing filter 51. That is to say, the polarization splitter 5 separates at least P-polarized light from light containing S-polarized light and P-polarized light.

The detection device 200 according to the modification of the second embodiment is for detecting moisture content in skin, and is optimally used to find moisture content in the stratum corneum (approximately 10 μm to 20 μm) of the skin. The state of the skin (moist state, dry state, chapped skin, etc.) can be detected from the moisture content in the stratum corneum. That is to say, the state of the skin can be detected from the moisture content of a relatively shallow portion of the skin. Accordingly, only P-polarized light is used in this modification. Other configurations of the modification of the second embodiment are the same as in the first embodiment. Configurations that are the same are denoted by the same reference numerals, and detailed description regarding these configurations will be omitted.

The control unit 7 calculates an index A that has correlation with moisture content, from information P1 and information P2 using Expression 1 (see Mutsuko Nakamura and Shigeki Nakauchi, "Moisturizing Effect of Skin Care Using NIR Imaging", Photonics 2010, Vol. 39 No. 11, PP 529-533)

$A = \text{Log}(P2/P1)$      Expression 1 where the index A is an index that is 0 in a state where an object is dry, and becomes larger than 0 the more moisture content the object contains.

The control unit 7 computes the moisture content of the object from the calculated index A, in accordance with calculation expressions and tables stored in the storage unit 11. The calculation expressions and tables may be calibration curves found from the ratio of light quantity between skin and moisture content, for example.

This detection device 200 can be worn on the body to detect the moisture content of the skin (the state of moisture in the skin). In this case, the human skin is the object. The photoreceptor 4 of the detection device 200 receives light that has reflected at the skin (the surface of the skin and the inside of the skin), and the control unit 7 calculates the moisture content of the skin from the intensity of light obtained via the photoreceptor 4.

Incident light to the skin becomes light that is reflected at the surface of the skin, and light that penetrates into the skin (approximately 10 μm to 20 μm) and is scattered. A great part of the light that scatters inside the skin exits in different directions from the direction of normal reflection of the light reflecting at the surface of the skin. Out of the light that has reflected at the skin, P-polarized light is received, so there is little reflection at the surface of the skin. Accordingly, the detection device 200 can detect just the moisture content of the skin by receiving reflected light that has penetrated slightly into the skin from the surface thereof.

Although P-polarized light is used to detect the state of the skin, but this is not indispensible, and S-polarized light may be used as well. It is sufficient to detect the moisture content for the state of the object, and there is no need to detect a frozen state.

Operations of Detection Device

Figure 7:
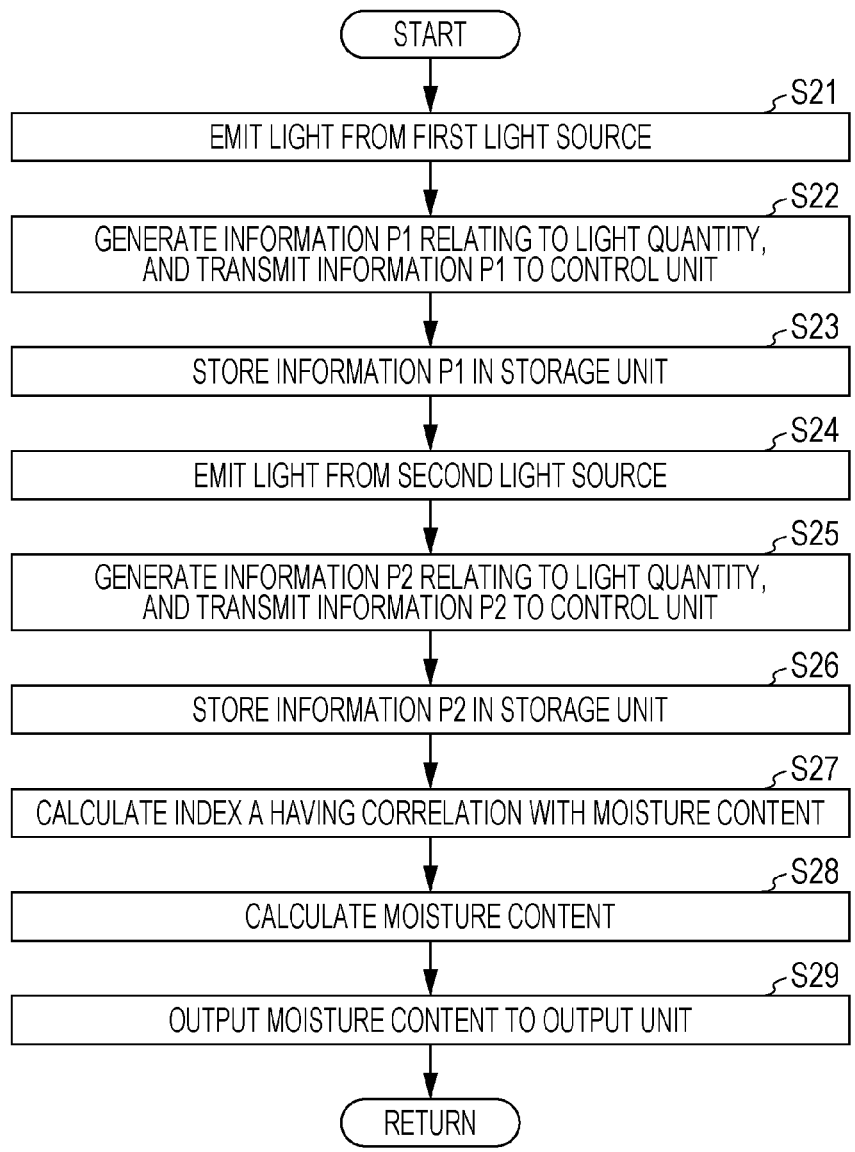
FIG. 7 is a flowchart illustrating operations of the detection device according to the modification of the second embodiment.

Next, an example of operations of the detection device 200 will be described with reference to FIG. 7. FIG. 7 is a flowchart illustrating the operations of the detection device 200 according to the modification of the second embodiment.

The detection device 200 is first worn on the body of the user to detect the moisture content in the skin. A dedicated program stored in the detection device 200 is then activated.

For example, in a case where light of P1 polarization intensity is to be received by the photoreceptor 4, the control unit 7 causes the first light source 31 to emit light of wavelength λ1, and light is cast on the skin (step S21). The light cast on the skin is scattered, and part of the light heads toward the P-polarizing filter 51 side. This light passes through the P-polarizing filter 51 and becomes P1 polarization intensity light, which is received at the photoreceptor 4. The photoreceptor 4 generates information P1 regarding the quantity of light that has been received, and transmits the information P1 to the control unit 7 (step S22). The control unit 7 then turns the first light source 31 off.

The control unit 7 receives the information P1 from the photoreceptor 4, and stores the information P1 in the storage unit 11 (step S23).

Next, in a case where light of P2 polarization intensity is to be received by the photoreceptor 4, the control unit 7 causes the second light source 32 to emit light of wavelength λ2, and light is cast on the skin (step S24). The light cast on the skin is scattered, and part of the light heads toward the P-polarizing filter 51 side. This light passes through the P-polarizing filter 51 and becomes P2 polarization intensity light, which is received at the photoreceptor 4. The photoreceptor 4 generates information P2 regarding the quantity of light that has been received, and transmits the information P2 to the control unit 7 (step S25). The control unit 7 then turns the second light source 32 off.

The control unit 7 receives the information P2 from the photoreceptor 4, and stores the information P2 in the storage unit 11 (step S26).

The control unit 7 then uses Expression 1 to calculate the index A that has correlation with the moisture content from the information P1 and information P2 (step S27). By adjusting the output of the first light source 31 and second light source 32 beforehand to where information P1 and information P2 are equal, the index A will be an index that is 0 in a state where an object is dry, and becomes larger than 0 the more moisture content the object contains.

Next, the control unit 7 computes the moisture content of the object from the calculated index A, in accordance with calculation expressions and tables stored in the storage unit 11 (step S28).

The control unit 7 then outputs the moisture content obtained in step S28 to the output unit 8 (step S29). The flow thus returns to the start, and continues the same detection. Other advantages of the modification of the second embodiment are the same as the advantages of the first embodiment and so forth.

Third Embodiment

A detection device 300 according to a third embodiment will now be described.

Configuration

Figure 8:
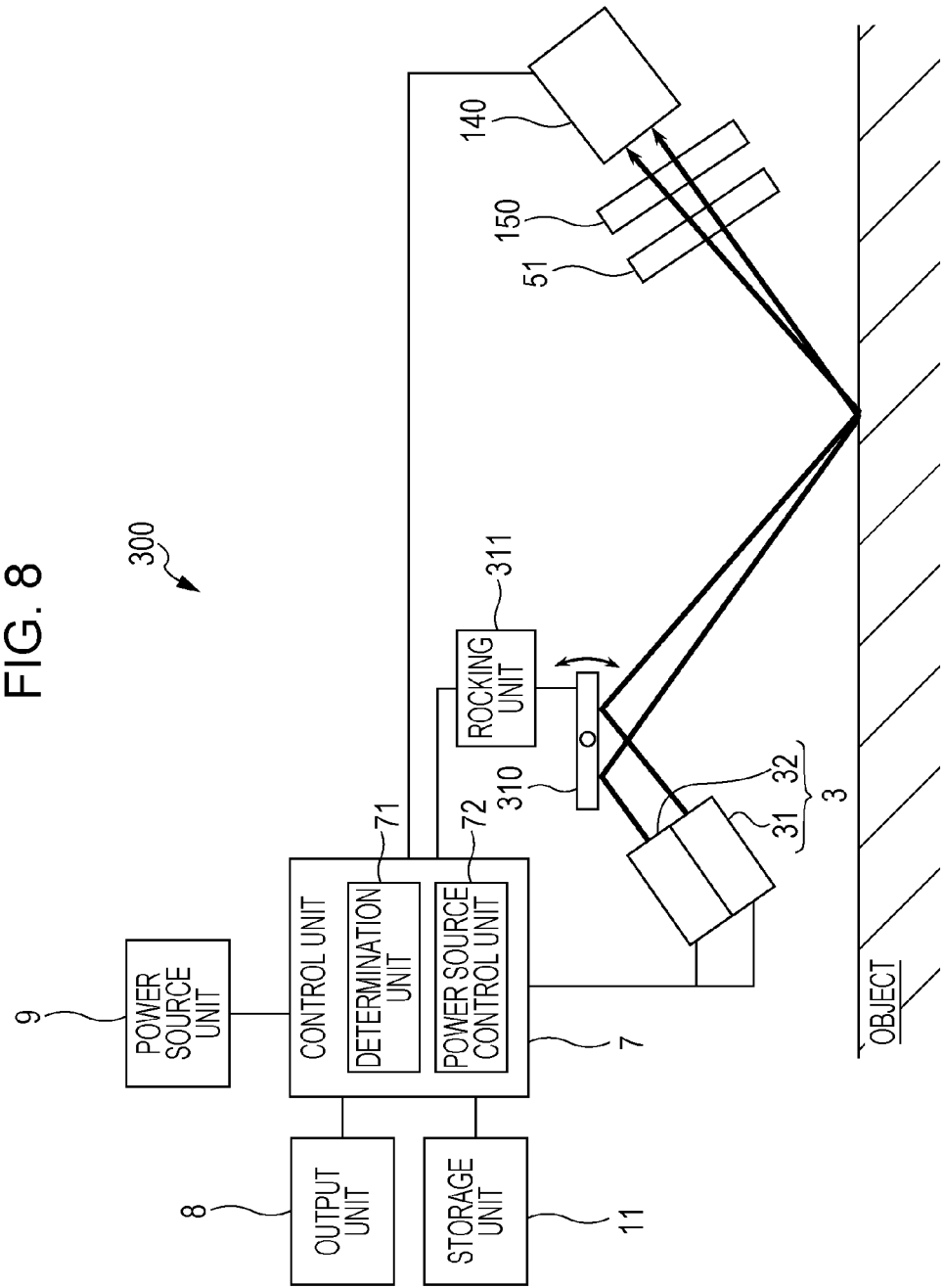
FIG. 8 is a schematic diagram illustrating a detection device according to a third embodiment.

The configuration of the detection device 300 according to the present embodiment will be described with reference to FIG. 8. FIG. 8 is a schematic diagram illustrating the detection device 300 according to the third embodiment.

The present embodiment differs from the second embodiment in that whereas the light of the light source 3 is directly cast on the object in the second embodiment, the light is cast on the object via a scanning mirror 310 (an example of a reflection plate). Another point that the present embodiment differs from the modification of the second embodiment is that a scattering plate 150 that scatters incident light is disposed between the camera 140 and the P-polarizing filter 51.

The camera 140 is disposed so as to receive light of normal reflection of the emitted light at the object, in the same way as the modification of the second embodiment. The camera 140 is used as an example of the photoreceptor 4 in the present embodiment. Other configurations of the present embodiment are the same as in the first embodiment and so forth. Configurations that are the same are denoted by the same reference numerals, and detailed description regarding these configurations will be omitted.

The scanning mirror 310 is a mirror that is capable of rocking, so as to distribute light from the light source 3 to different locations on the object, as illustrated in FIG. 8. The scanning mirror 310 may be a mirror where two Galvano mirrors have been combined, for example. Specifically, when light is emitted from the first light source 31, the control unit 7 scans the light cast on the object by reflecting the light from the light source 3 while rocking the scanning mirror 310. Rocking of the scanning mirror 310 is performed by a rocking unit 311 that has a drive mechanism. The scanning mirror 310 is rocked such that the light being scanned is cast within a predetermined range of the object. Although the scanning mirror 310 is rocked in the present embodiment, a configuration may be made where the first light source 31 and second light source 32 are rocked.

A neutral density (ND) filter may be disposed between the scattering plate 150 and the photoreceptor 4. The camera 140 may receive light via the scattering plate 150 and ND filter.

According to this detection device 300, light emitted from the first light source 31 and second light source 32 is reflected at the scanning mirror 310, scattered at the object, and received by the camera 140 via the P-polarizing filter 51 and scattering plate 150. Specifically, only the P-polarized light of the light reflected at the object via the scanning mirror 310 is transmitted through the P-polarizing filter 51, input to the scattering plate 150, and scattered. The camera 140 detects the light scattered at the scattering plate 150. Light scattered at the object is also input to the scattering plate 150, besides light that has reflected at the object. The light that has passed through and is leaving the scattering plate 150 contains luminescence spots with strong intensity that are due to reflected light, and luminescence spots with weak intensity that are due to light scattered at the object. The control unit 7 may store just information of the luminescence spots with strong intensity, out of the information obtained from the camera 140.

Operations the same as in the flowchart in FIG. 2 are performed with this detection device 300 as well.

Advantages of the Third Embodiment

Next, the advantages of the detection device 300 according to the present embodiment will be described. As described above, the detection device 300 according to the present embodiment further includes the scanning mirror 310 for reflecting light from the light source 3 toward the object, and the rocking unit 311 that rocks at least one of the scanning mirror 310 and the light source 3 so as to scan the light reflected at the scanning mirror 310 over the object.

According to this configuration, the state of the object can be detected over a wider range, as compared to a configuration where at least one of the scanning mirror 310 and the light source 3 is not rocked.

The detection device 300 according to the present embodiment further includes the scattering plate 150 that scatters light, between the object and the photoreceptor 4. The photoreceptor 4 receives light via the scattering plate 150.

According to this configuration, the control unit 7 recognizes luminescence spots with strong intensity that are due to reflected light and luminescence spots with weak intensity that are due to light scattered at the object. Accordingly, the control unit 7 can detect the distribution of moisture content of the object.

Particularly, the photoreceptor 4 in the detection device 300 according to the present embodiment is the camera 140. The camera 140 receives light via the scattering plate 150.

According to this configuration, luminescence spots with strong intensity that are due to reflected light, and luminescence spots with weak intensity that are due to light scattered at the object and so forth, are recognized as image information. Thus, the control unit 7 can perform detection from image information indicating the moisture content of the object, representing luminescence spots with strong intensity and luminescence spots with weak intensity.

The detection device 300 according to the present embodiment may include an ND filter between the scattering plate 150 and the photoreceptor 4. The camera 140 may receive light via the scattering plate 150 and the ND filter.

According to this configuration, the ND filter allows passage only of light with luminescence spots with strong intensity, out of the light where luminescence spots with strong intensity and luminescence spots with weak intensity have been separated. Accordingly, detection can be made in a sure manner from image information indicating the moisture content of the object.

Particularly, an arrangement may be made where the intensity of light of the entire face of the scattering plate 150 is detected using a single-pixel photoreceptor 4 instead of the camera 140. In this case, simply providing the ND filter allows only light with strong intensity to be transmitted out of the light from the scattering plate 150. Accordingly, the moisture content of the object can be detected in a sure manner with a simple configuration. Other advantages of the present embodiment are the same as the advantages of the first embodiment and so forth.

Fourth Embodiment

Figure 9:
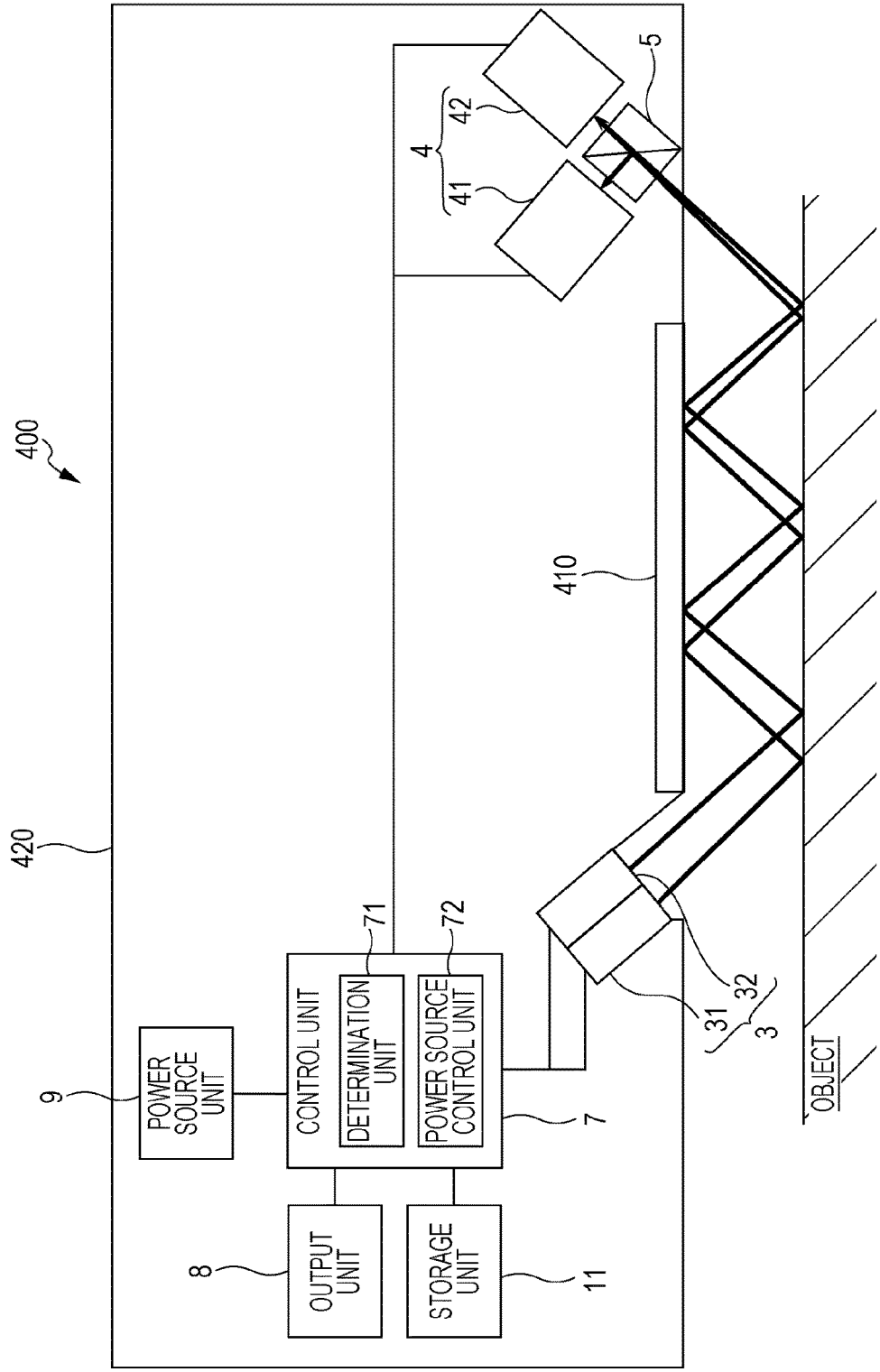
FIG. 9 is a schematic diagram illustrating a detection device according to a fourth embodiment.

A detection device 400 according to a fourth embodiment will now be described.
Configuration The configuration of the detection device 400 according to the present embodiment will be described with reference to FIG. 9. FIG. 9 is a schematic diagram illustrating the detection device 400 according to the fourth embodiment. The present embodiment differs from the second embodiment with regard to the point that a reflection mirror 410 is provided, and light that has been reflected via the reflection mirror 410 and the object is received. Other configurations of the present embodiment are the same as in the first embodiment and so forth. Configurations that are the same are denoted by the same reference numerals, and detailed description regarding these configurations will be omitted.

The detection device 400 according to the present embodiment further includes an encasement 420 and the reflection mirror 410, in addition to the first light source 31, second light source 32, control unit 7, storage unit 11, power source unit 9, polarization splitter 5, first photoreceptor 41, and second photoreceptor 42, of the second embodiment, as illustrated in FIG. 9.

The encasement 420 is a box-shaped member that accommodates the first light source 31, second light source 32, control unit 7, storage unit 11, power source unit 9, polarization splitter 5, first photoreceptor 41, second photoreceptor 42, reflection mirror 410, and so forth. The first light source 31 and second light source 32 are disposed within the encasement 420 such that light is cast toward the object.

The reflection mirror 410 is disposed facing the object. Specifically, the reflection mirror 410 is provided such that light from the first light source 31 and second light source 32 is reflected once or more at each of the object and the reflection mirror 410. The optical axes of the first light source 31 and second light source 32 may be directed toward the reflection mirror 410. That is to say, it is sufficient for reflection to occur once or more at each of the object and the reflection mirror 410. The photoreceptor 4 may receive light that has diffused at the object.

According to this detection device 400, the light emitted from the first light source 31 and second light source 32 travels toward the first photoreceptor 41 and second photoreceptor 42 while reflecting once or more at each of the object and the reflection mirror 410. The first photoreceptor 41 and second photoreceptor 42 receives the light after reflection between the reflection mirror 410 and the object via the polarization splitter 5.

Operations the same as in the flowchart in FIG. 2 are performed with this detection device 400 as well.

Advantages of the Fourth Embodiment

Advantages of the detection device 400 according to the present embodiment will be described. The detection device 400 according to the present embodiment further includes the reflection mirror 410 that reflects light, and the encasement 420 accommodating the reflection mirror 410, light source 3, photoreceptor 4, polarization splitter 5, and determination unit 71, as described above. The reflection mirror 410 is provided to the encasement 420 such that reflection occurs once or more at each of the reflection mirror 410 and the object, in a state where the reflection mirror 410 faces the object.

According to this configuration, light repeatedly enters the object, so the state of the object can be detected more accurately, and detection capability reliability and sensitivity can be improved. Particularly, this is suitable to detect minute amounts of moisture in the object. Other advantages of the present embodiment are the same as the advantages of the first embodiment and so forth.

Modification of Fourth Embodiment

Figure 10:
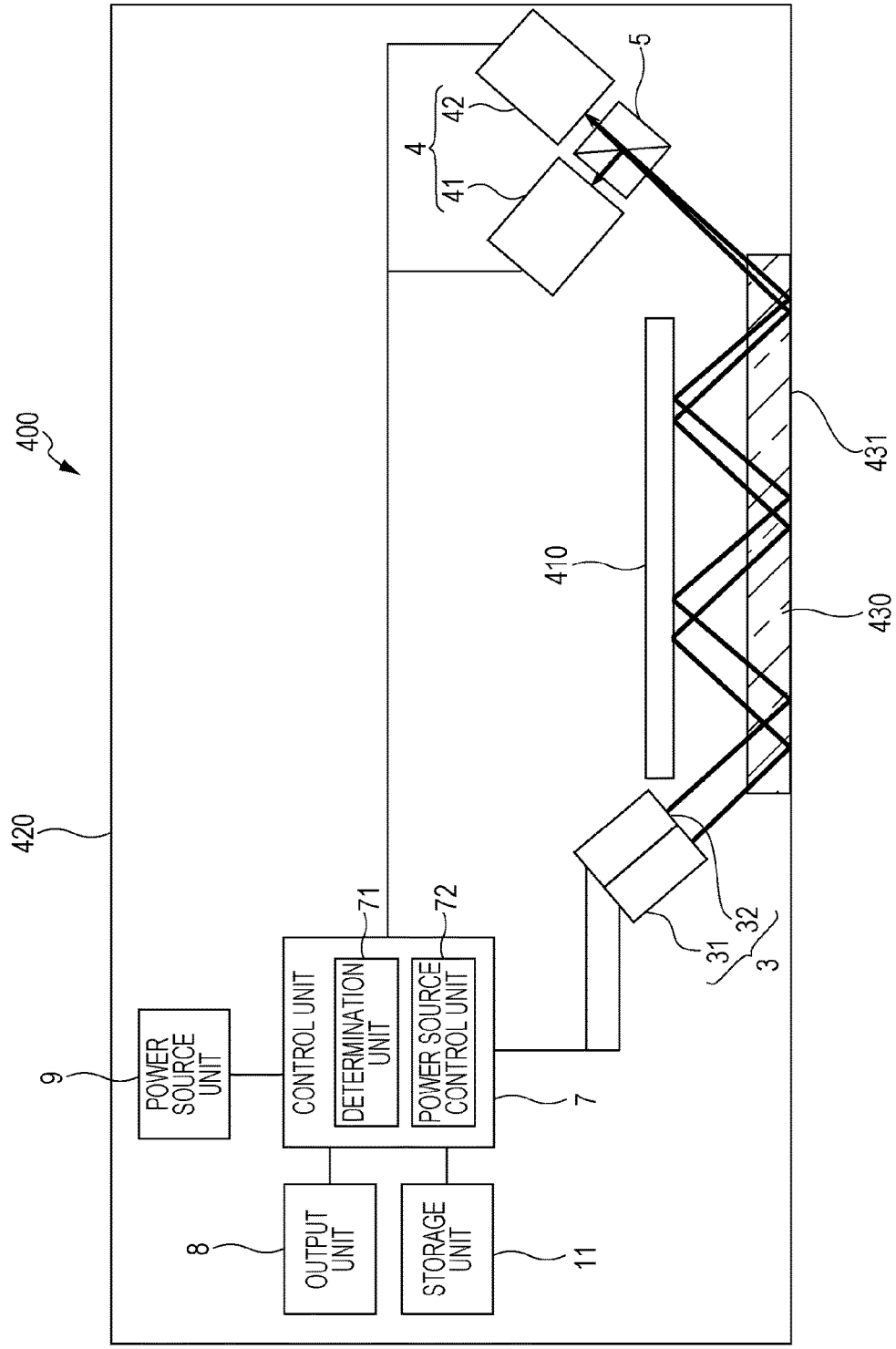
FIG. 10 is a schematic diagram illustrating a detection device according to a modification of the fourth embodiment.

A detection device 400 according to a modification of the fourth embodiment will be described with reference to FIG. 10. FIG. 10 is a schematic diagram illustrating the detection device 400 according to the modification of the fourth embodiment. The modification of the fourth embodiment differs from the fourth embodiment with regard to the point that a transmission plate 430 is disposed between the reflection mirror 410 and the object. Other configurations of the modification of the fourth embodiment are the same as in the first embodiment and so forth. Configurations that are the same are denoted by the same reference numerals, and detailed description regarding these configurations will be omitted.

The detection device 400 according to the modification of the fourth embodiment is disposed on a radiator grill or the like, of a vehicle for example. The detection device 400 further includes the transparent transmission plate 430 that transmits light, in addition to the first light source 31, second light source 32, control unit 7, storage unit 11, power source unit 9, polarization splitter 5, first photoreceptor 41, and second photoreceptor 42 as illustrated in FIG. 10.

The transmission plate 430 is provided to the encasement 420 in a state of being exposed from the outer peripheral face of the encasement 420. The transmission plate 430 has a boundary surface 431 that is a surface exposed from the encasement 420. Snow, rain, and the like adhere to the boundary surface 431. The object in the modification of the fourth embodiment is the rain, snow, and so forth, that has adhered to the transmission plate 430. Any sort of transmission plate 430 may be used, even of the absorbance of incident light is not 0, as long as the absorbance of the wavelength λ1 and the wavelength λ2 is approximately the same.

The first light source 31 and second light source 32 are disposed such that light emitted therefrom enters from the reflection mirror 410 side of the transmission plate 430, and reflects at the boundary surface 431. According to this detection device 400, light emitted from the first light source 31 and second light source 32 travels toward the first photoreceptor 41 and second photoreceptor 42 side while being reflected between the transmission plate 430 and the reflection mirror 410. Specifically, light that has entered the transmission plate 430 enters from the side of the transmission plate 430 toward the reflection mirror 410, is transmitted through the inside of the transmission plate 430, reflects at the boundary surface 431 of the transmission plate 430, and heads toward the reflection mirror 410. The same reflection is repeated as the light travels toward the first photoreceptor 41 and second photoreceptor 42. Note that the face of the transmission plate 430 toward the reflection mirror 410 is preferably coated with a non-reflective coating, so that light reflected at the boundary surface 431 does not reflect at the face of the transmission plate 430 toward the reflection mirror 410. In this case, reflection is suitably repeated between the boundary surface 431 of the transmission plate 430 and the reflection mirror 410.

For example, in a case where snow or rain or the like adheres to the boundary surface 431 of the transmission plate 430, light that has entered the boundary surface 431 is partially subjected to irregular reflection at the boundary surface 431, while another part of the light is refracted at the boundary surface 431 of the transmission plate 430. In a case where there is no adhesion of snow, rain, or the like, on the boundary surface 431, the light is subjected to normal reflection at the boundary surface 431. Thus, the detection device 400 can detect the object that has adhered to the boundary surface 431. Note that the surface of the boundary surface 431 may be coarse so as to enable irregular reflection, since there are cases where a film of ice may form on the boundary surface 431, for example. In the case of water, the interface with the outside will be generally flat, and normal reflection of light may occur at the interface.

Operations the same as in the flowchart in FIG. 2 are performed with this detection device 400 as well.

Advantages of the Modification of the Fourth Embodiment

Advantages of the detection device 400 according to the modification of the fourth embodiment will be described. The detection device 400 according to the modification of the fourth embodiment further includes the boundary surface 431 to which the object adheres, and the transmission plate 430 that transmits light. The transmission plate 430 is disposed with the boundary surface 431 exposed form the encasement 420 such that reflection occurs once or more at each of the transmission plate 430 and the reflection mirror 410.

According to this configuration, light repeatedly enters the boundary surface 431 of the transmission plate 430, so the boundary surface 431 of the transmission plate 430 serves as a detection surface, and detection capability reliability and sensitivity can be improved. Particularly, multiple reflection between the boundary surface 431 of the transmission plate 430 and the reflection mirror 410 enables the size of the detection device 400 to be reduced. Other advantages of the modification of the fourth embodiment are the same as the advantages of the first embodiment and so forth.

Fifth Embodiment

Figure 11:
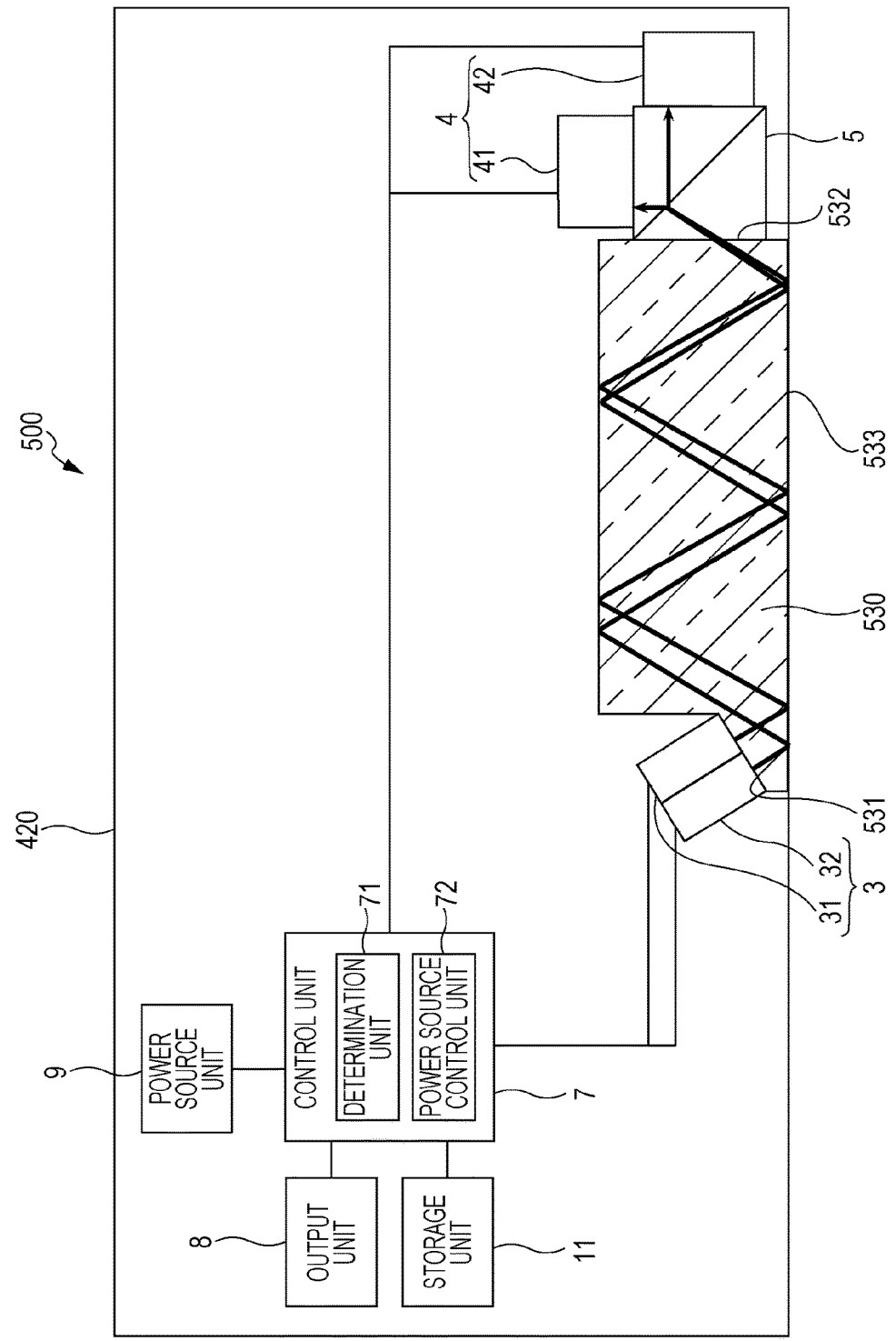
FIG. 11 is a schematic diagram illustrating a detection device according to a fifth embodiment.

A detection device 500 according to a fifth embodiment will be described with reference to FIG. 11.
Configuration The configuration of the detection device 500 according to the present embodiment will be described with reference to FIG. 11. FIG. 11 is a schematic diagram illustrating the detection device 500 according to the fifth embodiment. The present embodiment differs from the fourth embodiment in that a light guide 530 (an example of a transmission unit) has been provided instead of the reflection mirror 410 and transmission plate 430. Other configurations of the present embodiment are the same as in the first embodiment and so forth. Configurations that are the same are denoted by the same reference numerals, and detailed description regarding these configurations will be omitted.

The detection device 500 further includes the light guide 530, besides the first light source 31, second light source 32, control unit 7, storage unit 11, power source unit 9, polarization splitter 5, first photoreceptor 41, and second photoreceptor 42. The light guide 530 is a slender transparent member that has an entry face 531, an exit face 532, and a boundary surface 533. The first light source 31 and second light source 32 are provided to one end side of the light guide 530, so that light can enter from the entry face 531. The polarization splitter 5, first photoreceptor 41, and second photoreceptor 42 are provided at the other end side of the light guide 530, to receive light emitting from the exit face 532. The light guide 530 is disposed such that the boundary surface 533 is exposed from the peripheral face of the encasement 420. Examples of the material the light guide 530 is made of include multicomponent glass, quartz, resins such as plastic, etc. Alternatively, the light guide 530 may be a liquid light guide. The surface of the boundary surface 533 may also be coarse so as to enable irregular reflection.

In a case of using the detection device 500 in a vehicle, for example, snow, rain, and so forth adheres to the boundary surface 533, and in a case of using the detection device 500 to detect the moisture content of human skin, the skin comes into contact with the boundary surface 533. According to this detection device 500, light emitted from the first light source 31 and second light source 32 enters from the entry face 531 of the light guide 530, is transmitted through the light guide 530 while reflecting, and travels toward the side of the first photoreceptor 41 and second photoreceptor 42.

Operations the same as in the flowchart in FIG. 2 are performed with this detection device 500 as well.

Advantages of the Fifth Embodiment

Advantages of the detection device 500 according to the present embodiment will now be described. The detection device 500 further includes the boundary surface 533 to which the object adheres, and the light guide 530 through which light is transmitted, as described above. The light guide 530 guides incident light from the light source 3 to the photoreceptor 4 via the polarization splitter 5.

According to this configuration, light repeatedly enters the boundary surface 533 of the light guide 530, so the boundary surface 533 of the light guide 530 serves as a detection surface, and detection capability reliability and sensitivity can be improved. Particularly, multiple reflection within the light guide 530 enables the size of the detection device 500 to be reduced. Other advantages of the present embodiment are the same as the advantages of the first embodiment and so forth.

Sixth Embodiment

Figure 12:
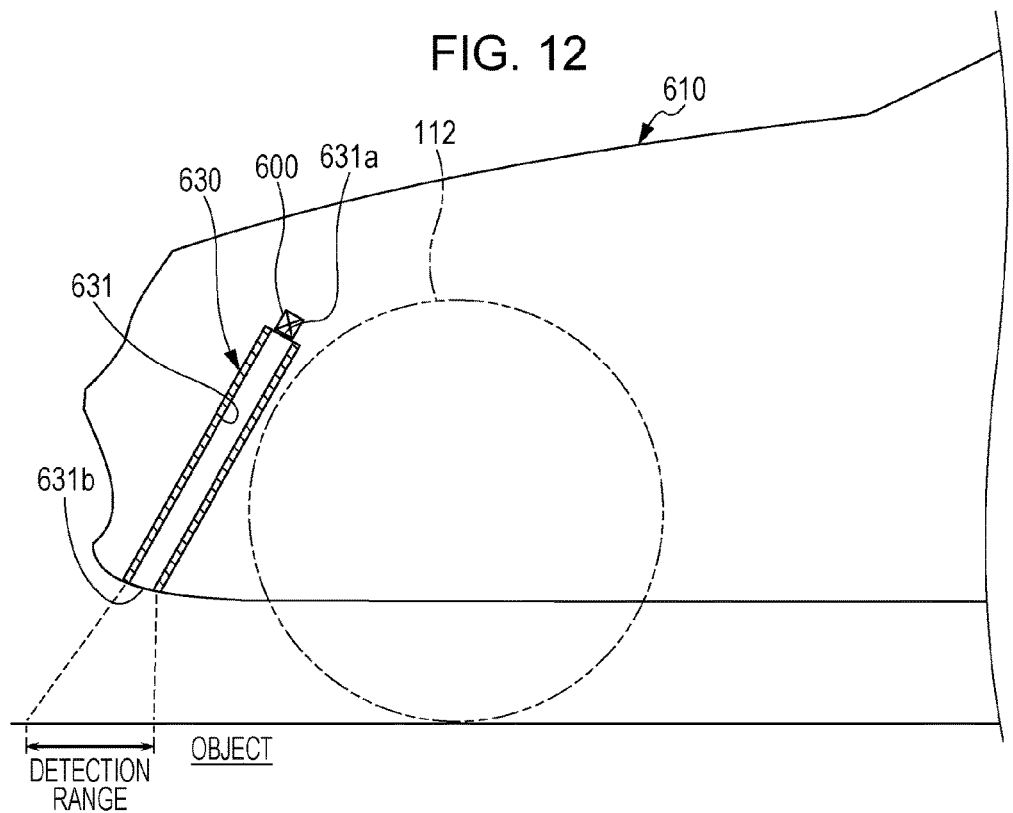
FIG. 12 is a schematic diagram illustrating a vehicle having a detection device according to a sixth embodiment.

A detection device 600 according to a sixth embodiment will be described next.
Configuration
The configuration of the detection device 600 according to the present embodiment will be described with reference to FIG. 12. FIG. 12 is a schematic diagram illustrating a vehicle 610 having the detection device 600 according to the sixth embodiment. An arrangement has been described in the modification of the first embodiment, where light of the light source 3 is cast in the direction of travel of the vehicle 110 to detect the state of the object, but the present embodiment differs from this in that the light of the light source 3 is cast beneath the vehicle 610 (the side toward the object) and the periphery thereof to detect the state of the object, and so forth. Other configurations of the present embodiment are the same as the modification of in the first embodiment and so forth. Configurations that are the same are denoted by the same reference numerals, and detailed description regarding these configurations will be omitted.

The vehicle 610 includes the detection device 600 and a tubular member 630, with the detection device 600 and tubular member 630 accommodated in the engine compartment for example, as illustrated in FIG. 12. It should be noted, however, that while the detection device 600 and tubular member 630 are accommodated in the engine compartment of the vehicle 610 in the present embodiment, this is not restrictive, and may be placed in any manner as long as the object beneath the vehicle 610 is detected.

The detection device 600 is disposed at one end side of the tubular member 630. That is to say, the detection device 600 is provided at the side of the tubular member 630 opposite from the object. The detection device 600 detects the object beneath the vehicle 610 via the tubular member 630. The object in the present embodiment is the road surface of a road, for example.

The detection device 600 detects the state of the object within detection range. This detection range is a range over which the state of the object can be detected, and is a range over which light is cast on the object. The detection range is the object situated beneath the vehicle 610 and at the periphery of beneath the vehicle 610. Specifically, the detection range is the object directly beneath the vehicle 610 and at the periphery of directly beneath the vehicle 610. An example of the detection range in the present embodiment is a range of light emitted from the other end side of the tubular member 630 and cast on the object.

The tubular member 630 has a tubular form that guides light emitted by the light source 3 of the detection device 600, and light reflected or scattered at the object. Although the tubular member 630 is provided to the vehicle 610 in a state inclined as to the vertical direction in the present embodiment, the angle of installation may be generally parallel to the vertical direction.

The tubular member 630 is a slender tube, having a guide hole 631, a one-end opening 631a, and an other end opening 631b. The guide hole 631 passes from one end side to the other end side. The one end side of the guide hole 631 is the one-end opening 631a, and the other end side of the guide hole 631 is the other end opening 631b. The one end side is the upper side in the present embodiment, and the other end side is the lower side. The detection device 600 is provided near the one-end opening 631a so as to be capable of emitting and receiving light (detecting the state of the object via the tubular member 630). The other end opening 631b faces the object side, and is continuous with the outside of the vehicle 610. The face that forms the guide hole 631 is a light-reflecting face that reflect light, such as a face that exhibits mirror reflection, for example.

Although the tubular member 630 according to the present embodiment is a cylinder having a circular cross-section, this is not restrictive. It is sufficient that the tubular member 630 be tubular in form, and may have a polygonal cross-section, or the like. Also, though the diameter of the tubular member 630 is constant in the present embodiment, the diameter may gradually increase the farther away from the detection device 600. That is to say, an arrangement may be made where the object side of the tubular member 630 is large in diameter, and the detection device 600 side of the tubular member 630 is small in diameter.

In a case of detecting the state of an object using such a detection device 600, the light source 3 of the detection device 600 cases light onto the object through (via) the guide hole 631 of the tubular member 630. The photoreceptor 4 of the detection device 600 then receives light, which has reflected or scattered at the object, through (via) the guide hole 631 of the tubular member 630. Operations of the detection device 600 are the same as the first embodiment and so forth, so description thereof will be omitted.

Figure 13:
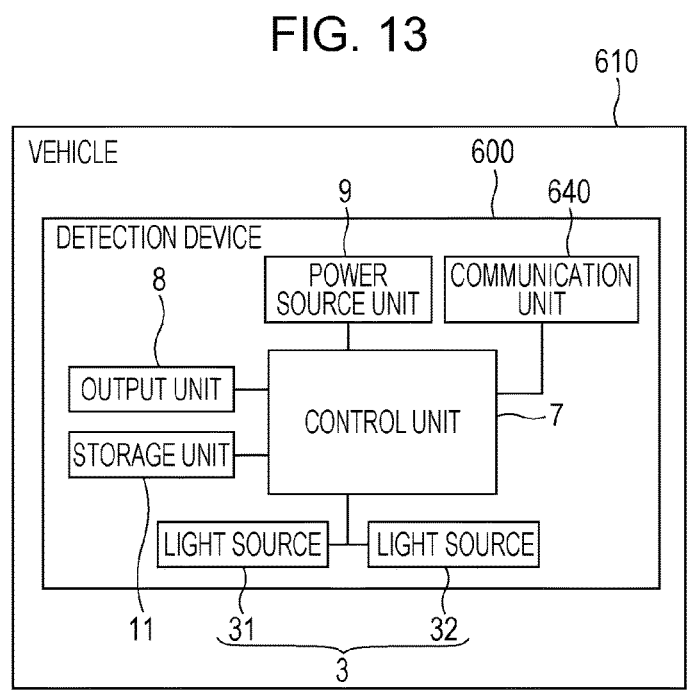
FIG. 13 is a block diagram illustrating the vehicle in a vehicle support system according to the sixth embodiment.
Figure 14:
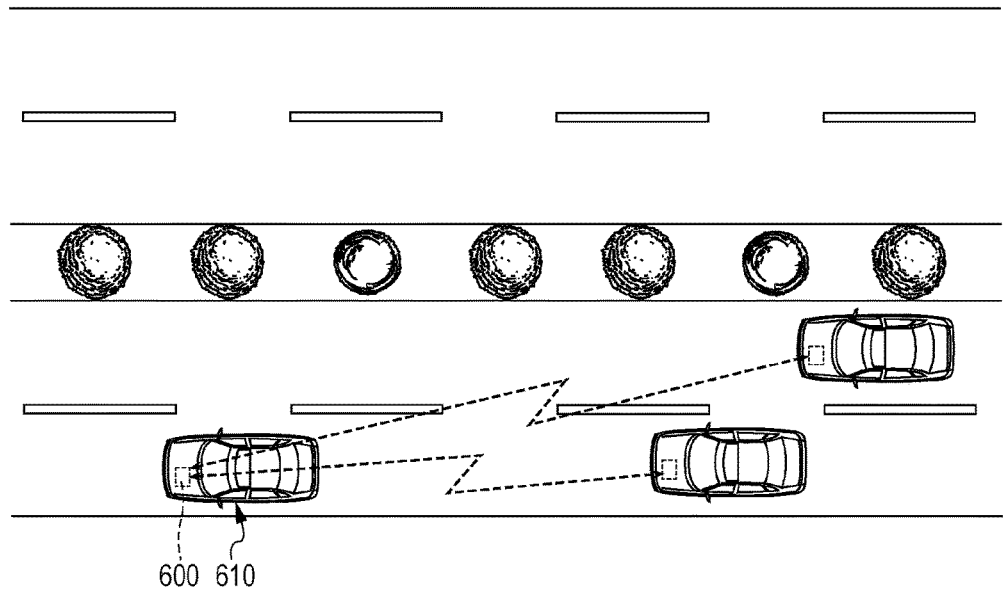
FIG. 14 is a schematic diagram illustrating the vehicle support system according to the sixth embodiment.

FIG. 13 is a block diagram illustrating the vehicle 610 in a vehicle support system according to the sixth embodiment, and FIG. 14 is a schematic diagram illustrating the vehicle support system according to the sixth embodiment. The detection device 600 may make up the vehicle support system onboard the vehicle 610, as illustrated in FIG. 14. Although three vehicles 610 are illustrated as an example in the vehicle support system, the number is not restricted in particular.

The detection device 600 includes a communication unit 640, in addition to the light source 3, control unit 7, storage unit 11, and power source unit 9, as illustrated in FIG. 13. The communication unit 640 is a device having an antenna and so forth, and can communicate with other vehicles 610.

The control unit 7 may frequently share position information with other vehicles 610 traveling on the same road, via the communication unit 640. For example, the control unit 7 may transmit information regarding the state of the object beneath the vehicle 610 and at the periphery of beneath the vehicle 610, to vehicles 610 traveling on the same road behind via the communication unit 640. In the present embodiment, the vehicle 610 may transmit information relating to the state of the object that the detection device 600 of a leading vehicle 610 has detected, to two vehicles 610 following behind. The two following vehicles 610 may receive this information via their communication units 640, and output this information at their output units 8. The two vehicles 610 following behind may further transmit information relating to the state of the object to other vehicles 610 even farther behind. In this case, the vehicles 610 behind can obtain information relating to the object from the leading vehicle 610, thereby facilitating danger avoidance of the vehicles 610. Note that the following vehicles 610 also detect the state of the object.

The detection device 600 may perform communication with the following vehicles 610 using an onboard antenna provided to a car navigation system. Accordingly, the communication unit 640 is not an indispensable component of the detection device 600.

Advantages of Sixth Embodiment

Next, advantages of the detection device 600 according to the present embodiment will be described. In the detection device 600 according to the present embodiment, the detection range where the detection device 600 detects the state of the object is the object situated beneath the vehicle 610 and at the periphery of beneath the vehicle 610, as described above.

According to this configuration, the distance between the detection range and the detection device 600 can be reduced as compared to a case where light is cast toward the direction of travel of the vehicle 610, since the state of the object beneath the vehicle 610 is detected. Accordingly, positional deviation of the detection range due to pitching of the vehicle 610 can be reduced.

Also, the vehicle 610 is provided with the tubular member 630 extending on the direction of the light source 3 casting light, in the detection device 600 according to the present embodiment. The detection device 600 detects the state of the object via the tubular member 630.

According to this configuration, the detection device 600 detects the state of the object via the tubular member 630, so the detection device 600 is farther away from the object in comparison with a case of directly attaching the detection device 600 to the lower face of the vehicle 610. This enables trouble, such as light not being able to be cast or received due to mud or the like flung up while traveling, or the detection device 600 being damaged due to flying rocks or the like, to be suppressed.

The object beneath the vehicle 610 faces the other end opening 631b of the tubular member 630 in the detection device 600, so it is less likely for water or snow to accumulate in the guide hole 631 of the tubular member 630 even in rainy or snowy conditions. Thus, erroneous detection by the detection device 600 can be suppressed.

Also, the inner face of the tubular member 630 has a light-reflecting face that reflects light in the detection device 600 according to the present embodiment.

According to this configuration, the light-reflecting face of the tubular member 630 reflects light, so usage efficiency of light passing through the tubular member 630 does not readily deteriorate. Other advantages of the present embodiment are the same as the advantages of the first embodiment and so forth.

Modification of Sixth Embodiment

Figure 15:
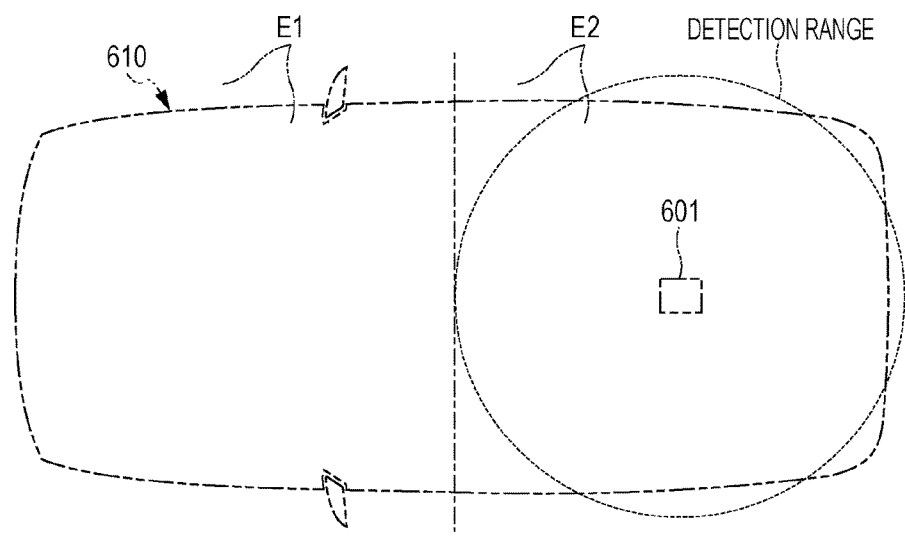
FIG. 15 is a schematic diagram illustrating a vehicle having a detection device according to a modification of the sixth embodiment.

A detection device 601 according to a modification of the present embodiment will be described with reference to FIG. 15. FIG. 15 is a schematic diagram illustrating a vehicle 610 having the detection device 601 according to the modification of the sixth embodiment. An arrangement has been described in the modification of the first embodiment, where light of the light source 3 is cast in the direction of travel of the vehicle 110 to detect the state of the object, but the modification of the sixth embodiment differs from this in that the light of the light source 3 is cast beneath the vehicle 610 and at the periphery of beneath the vehicle 610 to detect the state of the object and so forth. Other configurations of the present embodiment are the same as in the modification of the first embodiment and so forth. Configurations that are the same are denoted by the same reference numerals, and detailed description regarding these configurations will be omitted.

The single-dot line in FIG. 15 is a line sectioning the front side of the vehicle 610 (the side in the direction of travel of the vehicle 610) and the rear side (opposite side from the direction of travel of the vehicle 610), passing through the general middle in the length direction of the vehicle 610.

In the object situated beneath the vehicle 610 and at the periphery of beneath the vehicle 610, a region at the side in the direction of travel of the vehicle 610 is a first region E1, and a region at the opposite side from the direction of travel of the vehicle 610 is a second region E2, as illustrated in FIG. 15. The first region E1 and second region E2 are mutually different ranges. The detection range where the detection device 601 detects the state of the object is the second region E2 in the modification of the sixth embodiment. The detection range of the detection device 601 is indicated by a dotted line in FIG. 15, with part of the second region E2 being included in this detection range.

The detection device 601 is provided at the rear side of the vehicle 610 (opposite side from the direction of travel of the vehicle 610). Specifically, the detection device 601 is provided to detect the state of the object at the rear side of the vehicle 610, in the object situated beneath the vehicle 610 and at the periphery of beneath the vehicle 610. That is to say, the detection device 601 is provided to the vehicle 610 so as to detect the second region E2 that is the object situated beneath the vehicle 610 and at the periphery of beneath the vehicle 610. Note that the detection device 601 may detect the entire region of beneath the vehicle 610. Note that while the detection device 601 detects the state of the object in the second region E2, the state of the object in the first region E1 may further be detected.

In the detection device 601 according to the modification of the sixth embodiment, the object situated beneath the vehicle 610 and at the periphery of beneath the vehicle 610 has the first region E1 that is the side in the direction of travel of the vehicle 610, and the second region E2 that differs from the first region E1 and that is opposite side from the direction of travel of the vehicle 610. The detection range of the detection device 601 is the second region E2.

According to this arrangement where the detection device 601 is situated toward the rear side of the vehicle 610 to detect the second region E2, trouble, such as light not being able to be cast or received due to mud or the like flung up while the vehicle 610 is traveling, or the detection device 601 being damaged due to flying rocks or the like, can be suppressed.

Also, in a case where the vehicle 610 has a rearview camera, the state of the object in the range where the rear wheels are traveling can be detected when the vehicle 610 is moving in reverse (backing). The detection device 601 is particularly preferably installed at a position distanced from the wheels 112. Other advantages of the modification of the sixth embodiment are the same as the advantages of the first embodiment and so forth.

Seventh Embodiment

Figure 16:
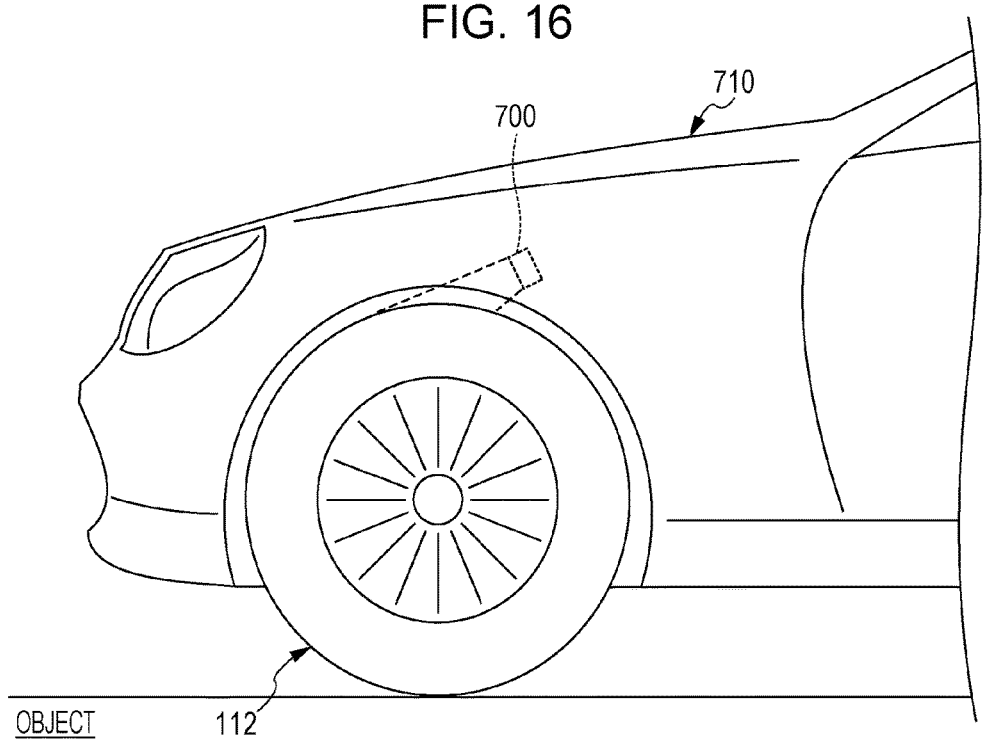
FIG. 16 is a schematic diagram illustrating a vehicle having a detection device according to a seventh embodiment.
Figure 17A:
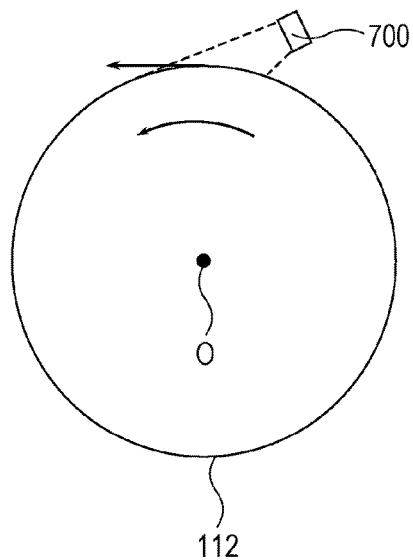
FIGS. 17A and 17B are schematic diagram, FIG. 17A illustrating a detection device according to the seventh embodiment and a wheel, and FIG. 17B illustrating a detection device according to a comparative example and a wheel.

A detection device 700 according to a seventh embodiment will now be described.
Configuration
The configuration of the detection device 700 according to the present embodiment will be described with reference to FIGS. 16 and 17A. FIG. 16 is a schematic diagram illustrating a vehicle 710 having the detection device 700 according to the seventh embodiment, and FIG. 17A is a schematic diagram illustrating the detection device 700 according to the seventh embodiment and a wheel 112. The straight arrow in FIG. 17A indicates the tangential direction following the direction of rotation of the wheel 112.

Although an arrangement has been described in the modification of the first embodiment, where light of the light source 3 is cast in the direction of travel of the vehicle 110 to detect the state of the object, the present embodiment differs from this in that the light of the light source 3 is cast toward the wheel 112 of the vehicle 610 to detect the state of the wheel 112 or the like. Other configurations of the present embodiment are the same as in the modification of the first embodiment and so forth. Configurations that are the same are denoted by the same reference numerals, and detailed description regarding these configurations will be omitted.

The detection device 700 is provided in the wheel well accommodating the wheel 112, to detect the state of the outer circumferential face (face coming in contact with the object when traveling (an example of a surface)) of the wheel 112 of the vehicle 710, as illustrated in FIGS. 16 and 17A. The detection device 700 is provided to the fender liner forming the wheel well, for example. The wheel 112 has a wheel connected to an axle rotating on an axial center O, and a tire provided on the outer circumference of the wheel. The position at which the detection device 700 is disposed is not restricted in particular in the present embodiment, since any arrangement is sufficient as long as the state of the outer circumferential face of the wheel 112 can be detected.

The detection device 700 is provided to the vehicle 710 so as to detect the state of the surface of the wheel 112. The direction in which the light of the light source 3 of the detection device 700 is cast is generally toward the direction of travel of the vehicle 710, as illustrated in FIG. 17A. Specifically, the light source 3 of the detection device 700 casts light along the tangential direction following the rotation direction of the wheel 112.

Comparative Example

Figure 17B:
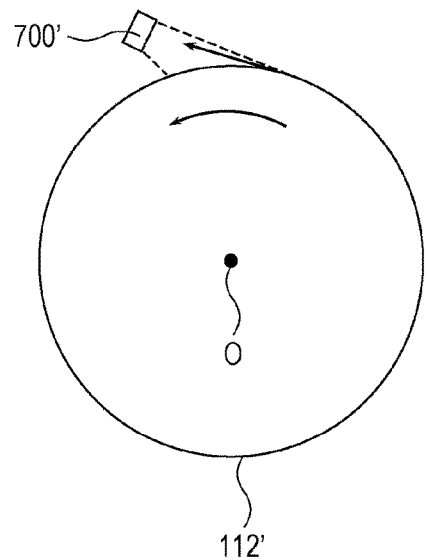

FIG. 17B is a schematic diagram illustrating a detection device 700' according to a comparative example and a wheel 112'. The straight arrow in FIG. 17B indicates the tangential direction following the direction of rotation of the wheel 112.

The detection device 700' is provided so that the direction of casting light of the light source 3 is against the tangential direction following the rotation direction of the wheel 112', as illustrated in FIG. 17B. In this case, mud, rocks, etc., that have adhered to the wheel 112' will fly in the tangential direction following the rotation direction of the wheel 112' when the wheel 112' is rotating. This causes trouble, such as light not being able to be cast or received due to mud flung up or the like, or the detection device 700' being damaged due to flying rocks or the like.

Advantages of Seventh Embodiment

Next, advantages of the detection device 700 according to the present embodiment will be described. The object of the detection device 700 according to the present embodiment is the wheel 112, as described above. The detection device 700 is provided to the vehicle 710 so as to be able to detect the state of the surface of the wheel 112.

According to this configuration, the detection device 700 can be situated at a position close to the wheel 112, so the light emission output of the light source 3 can be reduced as comparing with a case of casting light of the light source 3 in the direction of travel of the vehicle 110, as described in the modification of the first embodiment. Accordingly, conservation of energy can be realized with the detection device 700.

Further, the detection device 700 only needs to identify the tire of the wheel 112, and moisture and the like adhering to the tire, so there is no need to have highly-precise distinguishing accuracy, as compared to a case of identifying complicated materials such as asphalt and moisture and the like adhered to asphalt. Thus, increase in manufacturing costs of the detection device 700 can be suppressed.

Particularly, using this detection device 700 in the vehicle 710 enables whether or not there is moisture or the like between the road surface and the tire, so the gripping force of the tire can be comprehended more accurately. For example, even in a case where the vehicle 710 is traveling and leaves a frozen or snowy road or the like and is on a dry road, whether the tires are still wet from the previous road or the like can be comprehended.

The light source 3 of the detection device 700 according to the present embodiment emits light along the tangential direction following the rotation direction of the wheel 112.

According to this configuration, mud, rocks, etc., that have adhered to the wheel 112 flying in the tangential direction following the rotation direction of the wheel 112 when the wheel 112 is rotating will not readily strike the detection device 700, as illustrated in FIG. 17B. This enables trouble, such as light not being able to be cast or received due to mud flung or the like, or the detection device 700 being damaged due to flying rocks or the like, to be prevented. Other advantages of the present embodiment are the same as the advantages of the first embodiment and so forth.

Other Modifications, Etc.

Although the detection device, detection method, and detection program according to the present disclosure have been described by way of embodiments, the present disclosure is not restricted to the above-described embodiments. For example, in the configuration where the photoreceptor is disposed at the light source side as illustrated in FIG. 1, so that light scattered at the object can be received at the photoreceptor, increase in size of the detection device can be suppressed as compared with a case where the photoreceptor receives light of normal reflection at the object.

Also, the reflectance of P-polarized light at the water surface of water in the above embodiments is 0 when the incident angle is 53.1°. Accordingly, setting the incident angle of the emitted light to the object to be near 53.1° enables the ratio of intensity of P-polarized light and intensity of S-polarized light of the scattered light to be increased. In this case, the detection precision of the detection device can be improved.

The output unit in the above embodiments is not restricted to displaying a frozen state, a state under water, a state with snow accumulated, and a dry state, and may be a display unit that outputs text, video, and so forth. Further, the output unit may output audio and the like via a speaker or the like. In this case, applying the detection device to a vehicle enables safe driving support to be performed, since the state of the object in the periphery of the vehicle is detected, and the control unit notifies the passenger of the state of the surroundings via the output unit.

Also, in a case of applying the detection device to a vehicle in the above embodiments, the output unit may notify the passenger of the state of the object around the vehicle when the vehicle has stopped and the passenger is disembarking. This can help to suppress the passenger from falling when getting out of the vehicle in icy conditions or the like.

Also, in a case of applying the detection device to a vehicle in the above embodiments, the control unit may acquire information such as the state of driving of the vehicle, the state of seatbelt usage by the passengers, and so forth. In a case where a passenger is not using a seatbelt, the output unit may make notification to that effect.

In a case of detecting moisture content in human skin in the above embodiments, the control unit may store the moisture content of the skin that has been detected in the storage unit. The control unit may perform data comparison with data detected in the past, and output the results.

The detection device in the above embodiments may be used to detect the moisture content of human skin. That is to say, detection devices other than the modification of the second embodiment may also be used.

Although one or more aspects of the present disclosure has been described by way of embodiments, the present disclosure is not restricted to the embodiments. One skilled in the art will be able to make various modifications of the embodiments and combinations of components in different embodiments without departing from the spirit and scope of the present disclosure, and all such modifications and combinations are encompassed by one or more aspects.

For example, the components in the above embodiments may be realized by being configured of dedicated hardware, or by executing software programs appropriate for the components. The components may be realized by a program executing unit such as a central processing unit (CPU) or some other processor reading out and executing software programs recorded in a recording medium such as a hard disk or semiconductor memory or the like.

The present disclosure is applicable to a device for detecting a state of moisture content or the like at an object such as a road surface, human skin, or the like. In a case of installing in a vehicle, the present disclosure is applicable to a detection device, detection method, and detection program used to detect a frozen state, a state under water, a state with snow accumulated, or a dry state, of the road surface. In a case of application to detecting moisture content of human skin, the present disclosure is applicable to a detection device, detection method, and detection program used to detect a dry state or moist state of skin.

What is claimed is:

1. A detection method of detecting a state of an object using a detection device, the method comprising:

acquiring, from a photoreceptor, information based on S1 polarization intensity of S-polarized light of the first wavelength band, P1 polarization intensity of P-polarized light of the first wavelength band, S2 polarization intensity of S-polarized light of the second wavelength band, and P2 polarization intensity of P-polarized light of the second wavelength band;

determining, in a case where the S2 polarization intensity or the P2 polarization intensity is greater than a predetermined threshold value, that the state of the object is a snow-accumulated state;

determining, in a case where the S1 polarization intensity and the S2 polarization intensity are generally equal, or the P1 polarization intensity and the P2 polarization intensity are generally equal, that the state of the object is a dry state;

determining, in a case where the P2 polarization intensity is greater than the S2 polarization intensity and also a value obtained by dividing the S2 polarization intensity by the P2 polarization intensity is equal to or smaller than a predetermined value, that the state of the object is an under-water state; and determining, in a case where the P2 polarization intensity is greater than the S2 polarization intensity and also a value obtained by dividing the S2 polarization intensity by the P2 polarization intensity is greater than a predetermined value, that the state of the object is a frozen state.

2. A detection device comprising:
a light source that emits, toward an object, light of a first wavelength band, and light of a second wavelength band that is less readily absorbed by water than the light of the first wavelength band;
a polarization splitter that splits at least P-polarized light from light that includes S-polarized light and P-polarized light and that has been reflected or scattered at the object;
a photoreceptor that receives light reflected or scattered at the object via the polarization splitter; and
a control unit that determines a state of the object from information based on light received by the photoreceptor,
wherein the light emitted by the light source is random polarized light where the ratio of S-polarized light and P-polarized light is generally uniform;
wherein the control unit
acquires, from the photoreceptor, information based on S1 polarization intensity of S-polarized light of the first wavelength band, P1 polarization intensity of P-polarized light of the first wavelength band, S2 polarization intensity of S-polarized light of the second wavelength band, and P2 polarization intensity of P-polarized light of the second wavelength band,
determines, in a case where the S2 polarization intensity or the P2 polarization intensity is greater than a predetermined threshold value, that the state of the object is a snow-accumulated state,
determines, in a case where the S1 polarization intensity and the S2 polarization intensity are generally equal, or the P1 polarization intensity and the P2 polarization intensity are generally equal, that the state of the object is a dry state,
determines, in a case where the P2 polarization intensity is greater than the S2 polarization intensity and also a value obtained by dividing the S2 polarization intensity by the P2 polarization intensity is equal to or smaller than a predetermined value, that the state of the object is an under-water state, and
determines, in a case where the P2 polarization intensity is greater than the S2 polarization intensity and also a value obtained by dividing the S2 polarization intensity by the P2 polarization intensity is greater than a predetermined value, that the state of the object is a frozen state.

3. The detection device according to claim 2, further comprising:
a wavelength separator that separates the light of the first wavelength band and the light of the second wavelength band, from the light reflected or scattered at the object;
wherein the wavelength separator is disposed between the object and the photoreceptor.

4. The detection device according to claim 2, further comprising:
a reflection plate that reflects light from the light source toward the object; and
a rocking unit that rocks at least one of the reflection plate and the light source, to scan light reflected at the reflection plate on the object.

5. The detection device according to claim 2, further comprising:
a scattering plate that scatters light,
wherein the scattering plate is disposed between the object and the photoreceptor,
and wherein the photoreceptor receives light via the scattering plate.

6. The detection device according to claim 5, further comprising:
a neutral density (ND) filter,
wherein the ND filter is disposed between the scattering plate and the photoreceptor,
and wherein the photoreceptor receives light via the scattering plate and the ND filter.

7. The detection device according to claim 2, further comprising:
a reflection mirror that reflects light; and
an encasement accommodating the reflection mirror, the light source, the photoreceptor, the polarization splitter, and the control unit,
wherein the reflection mirror is disposed in the encasement in a state facing the object, in a manner where at least one reflection occurs between the reflection mirror and the object.

8. The detection device according to claim 7, further comprising:
a transmission plate that transmits light, the transmission plate having a boundary surface to which the object is adhered,
wherein the transmission plate is disposed with the boundary surface exposed from the encasement, in a manner where at least one reflection occurs between the transmission plate and the reflection mirror.

9. The detection device according to claim 2, further comprising:
a transmission unit that transmits light, the transmission unit having a boundary surface to which the object is adhered,
wherein the transmission unit guides incident light from the light source to the photoreceptor via the polarization splitter.

10. The detection device according to claim 2,
wherein the light source includes a first light source that emits light of the first wavelength band and a second light source that emits light of the second wavelength band,
and wherein the control unit controls the first light source and the second light source so that the first light source and second light source are turned on and off alternately.

11. The detection device according to claim 2,
wherein light emitted from the light source is infrared light,
wherein infrared light of the first wavelength band is light having an absorption peak of an absorption wavelength as to water out of one of near 740 nm, 980 nm, 1450 nm, and 1940 nm,
and wherein infrared light of the second wavelength band is light of which the wavelength is shorter than the infrared light of the first wavelength band.

12. The detection device according to claim 2,
wherein the photoreceptor is a camera.

13. The detection device according to claim 12, further comprising:
an output unit that outputs a state of the object,
wherein the light source emits infrared light and visible light,
wherein the camera generates and transmits to the control unit
a first image where the object has been imaged, when the light source has emitted infrared light, a second image where the object has been imaged, when the light source has emitted visible light, and wherein the control unit generates a third image where the first image is overlaid on the second image received from the camera, and outputs the third image to the output unit.

14. The detection device according to claim 13, wherein the camera generates a fourth image indicating a distance between the object and the camera in the second image, and transmits to the control unit, and wherein the control unit generates a fifth image, where the fourth image received from the camera is overlaid on the third image, and outputs the fifth image to the output unit.

15. The detection device according to claim 2, wherein the detection device is installed in a vehicle, wherein the vehicle includes wheels steered by a steering wheel, a steering angle detection unit that detects a steering angle of the wheels, and a speed detection unit that detects a traveling speed of the vehicle, wherein the steering angle detecting unit transmits first information relating to the steering angle of the wheels to the control unit, wherein the speed detection unit transmits second information relating to the traveling speed of the vehicle to the control unit, and wherein the control unit effects control to change a direction in which the light source casts light and a position at which the object is imaged, in accordance with the first information and the second information.

16. The detection device according to claim 15, wherein a detection range where the detection device detects a state of the object is the object situated beneath the vehicle and the periphery of beneath the vehicle.

17. The detection device according to claim 16, wherein the object situated beneath the vehicle and the periphery of beneath the vehicle includes a first region in the direction of travel of the vehicle, and a second region that is different from the first region in the opposite side from the direction of travel of the vehicle, and wherein the detection range of the detection device is the second region.

18. The detection device according to claim 16, wherein the vehicle is provided with a tubular member that extends in the direction in which the light source casts light, and wherein the detection device detects a state of the object via the tubular member.

19. The detection device according to claim 18, wherein an inner face of the tubular member has a light-reflecting face that reflects light.

20. The detection device according to claim 15, wherein the object is the wheels, and wherein the detection device is installed in the vehicle so as to detect a state of a surface of the wheels.

21. The detection device according to claim 20, wherein the light source casts light along a tangential direction following a rotation direction of the wheels.

22. The detection device according to claim 15, wherein the control unit effects control where the greater the steering angle of the wheels is, the farther away from the detection device the object caused to be imaged by the photoreceptor is.

23. The detection device according to claim 22, wherein the control effects control where the faster the traveling speed of the vehicle is, the farther away from the detection device the object caused to be imaged by the photoreceptor is, in the direction of travel of the vehicle that the steering angle detection unit has detected from the steering angle of the wheels.

24. The detection device according to claim 2, wherein the light source simultaneously emits, toward the object, the light of the first wavelength band and the light of the second wavelength band, and wherein the light, reflected or scattered at the object, includes the light of the first wavelength band and the light of the second wavelength band.

25. The detection device according to claim 2, wherein the light source alternatively emits, toward the object, the light of the first wavelength band and the light of the second wavelength band, wherein the light, reflected or scattered at the object, is the light of the first wavelength band when the light source emits, toward the object, the light of the first wavelength band, and wherein the light, reflected or scattered at the object, is the light of the second wavelength band when the light source emits, toward the object, the light of the second wavelength band.

26. The detection device according to claim 2, wherein the light of the first wavelength band is random polarized light where the ratio of S-polarized light and P-polarized light is generally uniform, and wherein the light of the second wavelength band is random polarized light where the ratio of S-polarized light and P-polarized light is generally uniform.

27. A non-transitory computer-readable recording medium storing a program causing a computer to execute detection method of detecting a state of an object using a detection device, the method comprising:

acquiring, from a photoreceptor, information based on S1 polarization intensity of S-polarized light of the first wavelength band, P1 polarization intensity of P-polarized light of the first wavelength band, S2 polarization intensity of S-polarized light of the second wavelength band, and P2 polarization intensity of P-polarized light of the second wavelength band;

determining, in a case where the S2 polarization intensity or the P2 polarization intensity is greater than a predetermined threshold value, that the state of the object is a snow-accumulated state;

determining, in a case where the S1 polarization intensity and the S2 polarization intensity are generally equal, or the P1 polarization intensity and the P2 polarization intensity are generally equal, that the state of the object is a dry state;

determining, in a case where the P2 polarization intensity is greater than the S2 polarization intensity and also a value obtained by dividing the S2 polarization intensity by the P2 polarization intensity is equal to or smaller than a predetermined value, that the state of the object is an under-water state; and determining, in a case where the P2 polarization intensity is greater than the S2 polarization intensity and also a value obtained by dividing the S2 polarization intensity by the P2 polarization intensity is greater than a predetermined value, that the state of the object is a frozen state.

* * * * *